(12) United States Patent
Savran et al.

(10) Patent No.: US 12,331,312 B2
(45) Date of Patent: Jun. 17, 2025

(54) DETERMINISTIC CULTURING OF SINGLE CELLS

(71) Applicant: Purdue Research Foundation, West Lafayette, IN (US)

(72) Inventors: Cagri A. Savran, West Lafayette, IN (US); Rohil Jain, West Lafayette, IN (US); Chun-Li Chang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 402 days.

(21) Appl. No.: 17/225,708

(22) Filed: Apr. 8, 2021

(65) Prior Publication Data

US 2021/0380934 A1    Dec. 9, 2021

Related U.S. Application Data

(60) Provisional application No. 63/036,060, filed on Jun. 8, 2020.

(51) Int. Cl.

| C12N 5/00 | (2006.01) |
| C12M 1/00 | (2006.01) |
| C12M 1/36 | (2006.01) |
| C12M 3/00 | (2006.01) |
| C12M 3/06 | (2006.01) |
| C12N 5/071 | (2010.01) |
| C12N 5/09 | (2010.01) |
| G01N 33/50 | (2006.01) |

(52) U.S. Cl.
CPC ........... *C12N 5/0062* (2013.01); *C12M 21/08* (2013.01); *C12M 23/16* (2013.01); *C12M 23/34* (2013.01); *C12M 41/48* (2013.01); *C12N 5/0693* (2013.01); *C12N 5/0697* (2013.01); *G01N 33/5011* (2013.01); *G01N 33/5088* (2013.01); *C12N 2513/00* (2013.01)

(58) Field of Classification Search
CPC .. C12N 5/0062; C12N 5/0693; C12N 5/0697; C12N 2513/00; C12M 21/08; C12M 23/16; C12M 23/34; C12M 41/48; G01N 33/5011; G01N 33/5088
See application file for complete search history.

(56) References Cited

PUBLICATIONS

Chen, H., et al., "High-throughput, deterministic single cell trapping and long-term clonal cell culture in microfluidic devices," Lab on a Chip 15(4): 1072-1083. doi: 10.1039/c4lc01176g (Year: 2015).*
Aisenbrey, E. A., and Murphy, "Synthetic alternatives to Matrigel," Nature Reviews Materials. 5(7): 539-551. doi: 10.1038/s41578-020-0199-8. Epub May 27, 2020. (Year: 2020).*
Guan, Z., et al., "Facile and rapid generation of large-scale microcollagen gel array for long-term single-cell 3D culture and cell proliferation heterogeneity analysis," Analytical Chemistry 86(5): 2789-2797. doi: 10.1021/ac500088m. Epub Feb. 18, 2014. (Year: 2014).*
Mao, A. S., et al., "Deterministic encapsulation of single cells in thin tunable microgels for niche modelling and therapeutic delivery," Nature Materials 16(2): 236-243. doi: 10.1038/nmat4781. Epub Oct. 31, 2016. (Year: 2016).*
Huang et al., "A microfluidic microwell device for immunomagnetic single-cell trapping," Microfluidics and Nanofluidics 22, 16. https://doi.org/10.1007/s10404-018-2040-x (Year: 2018).*
Fang, Y., and Eglen, R. M., "Three-Dimensional Cell Cultures in Drug Discovery and Development" SLAS Discovery 22(5): 456-472. doi: 10.1177/1087057117696795. Published online May 18, 2017 (Year: 2017).*
Warmflash, A., et al., "A method to recapitulate early embryonic spatial patterning in human embryonic stem cells," Nat Methods 11(8): 847-854. doi: 10.1038/nmeth.3016. Epub Jun. 29, 2014. (Year: 2014).*
Wang, H., et al., "Bioinspired One Cell Culture Isolates Highly Tumorigenic and Metastatic Cancer Stem Cells Capable of Multilineage Differentiation," Adv Sci 7(11): 2000259. doi: 10.1002/advs.202000259. Apr. 28, 2020. (Year: 2020).*
Ratajczak, M. Z., et al., "Very small embryonic/epiblast-like stem cells: a missing link to support the germ line hypothesis of cancer development?," Am J Pathol 174(6): 1985-1992. doi: 10.2353/ajpath.2009.081143. (Year: 2009).*
Kang, J., et al., "Mini-pillar array for hydrogel-supported 3D culture and high-content histologic analysis of human tumor spheroids," Lab Chip 16(12): 2265-2276. doi: 10.1039/c6lc00526h. (Year: 2016).*
Acerbi et al., "Human breast cancer invasion and aggression correlates with ECM stiffening and immune cell infiltration," Integrative Biology, Oct. 5, 2015, 7(10):1120, 16 pages.
Albini et al., "A rapid in vitro assay for quantitating the invasive potential of tumor cells. Cancer research," Jun. 15, 1987, 47(12):3239-45.
Aref et al., "Bowden M. 3D microfluidic ex vivo culture of organotypic tumor spheroids to model immune checkpoint blockade," Lab on a Chip, Sep. 2018, 18(20):3129-43.
Baccelli et al., "Identification of a population of blood circulating tumor cells from breast cancer patients that initiates metastasis in a xenograft assay," Nature Biotechnology, Jun. 2013, 31(6):539-44.
Beca et al., "Intratumor heterogeneity in breast cancer," Novel Biomarkers in the Continuum of Breast Cancer, Mar. 2016, 169-89.
Bianchi, "Fetal cells in the maternal circulation: feasibility for prenatal diagnosis," British Journal of Haematology, Jun. 1999, 105(3):574-83.
Brauchle et al., "Biomechanical and biomolecular characterization of extracellular matrix structures in human colon carcinomas," Matrix Biology, Aug. 1, 2018, 68:180, 37 pages.

(Continued)

*Primary Examiner* — Tracy Vivlemore
*Assistant Examiner* — Eric J Rogers
(74) *Attorney, Agent, or Firm* — Fish & Richardson P.C.

(57) ABSTRACT

The application relates to methods and systems for culturing individually selected cells in relative isolation from the rest of a population of cells, under physiologically relevant and controllable environmental conditions that can be designed to mimic specific environments, e.g., within a human body.

18 Claims, 17 Drawing Sheets

(56) References Cited

PUBLICATIONS

Celià-Terrassa et al., "Distinctive properties of metastasis-initiating cells," Genes & Development, Apr. 15, 2016, 30(8):892-908.
Chen et al., "Microfluidic array for three-dimensional perfusion culture of human mammary epithelial cells." Biomedical Microdevices, Aug. 2011, 13(4):753-8.
Chen et al., "Organotropism: new insights into molecular mechanisms of breast cancer metastasis," NPJ Precision Oncology, Feb. 16, 2018, 2(1), 12 pages.
Chen et al., "Single cell dual adherent-suspension co-culture microenvironment for studying tumor-stromal interactions with functionally selected cancer stem-like cells," Lab on a Chip, Jun. 2016, 16(15):2935-45.
Chen et al.., "Rare cell isolation and analysis in microfluidics," Lab on a Chip, Jan. 2014, 14(4):626-45.
Cheng et al., "Scaling and automation of a high-throughput single-cell-derived tumor sphere assay chip," Lab on a Chip, Oct. 2016, 16(19):3708-17.
Chittiboyina et al., "Gradient-on-a-Chip with reactive oxygen species reveals thresholds in the nucleus response of cancer cells depending on the matrix environment," ACS Biomaterials Science & Engineering, Feb. 12, 2018, 4(2):432, 29 pages.
Comet et al., "Maintaining cell identity: PRC2-mediated regulation of transcription and cancer," Nature Reviews Cancer, Dec. 2016, 16(12):803-10.
Corvaisier et al., "Regulation of cellular quiescence by YAP/TAZ and Cyclin El in colon cancer cells: Implication in chemoresistance and cancer relapse," Oncotarget, Aug. 30, 2016, 7(35):56699, 14 pages.
Crowley et al., "Analyzing cell death by nuclear staining with Hoechst 33342," Cold Spring Harbor Protocols, Sep. 1, 2016, 2016(9):pdb-rot087205, 5 pages.
Dagogo-Jack et al., "Tumour heterogeneity and resistance to cancer therapies," Nature Reviews Clinical Oncology, Feb. 2018, 15(2):81-94.
Davis et al., "Tumor dormancy and slow-cycling cancer cells," Human Cell Transformation, 2019 199-206.
Deng et al., "Single cell mutational analysis of PIK3CA in circulating tumor cells and metastases in breast cancer reveals heterogeneity, discordance, and mutation persistence in cultured disseminated tumor cells from bone marrow," BMC Cancer, Dec. 2014, 14(1), 12 pages.
Edmondson et al., "Three-dimensional cell culture systems and their applications in drug discovery and cell-based biosensors," Assay and Drug Development Technologies, May 1, 2014, 12(4):207, 12 pages.
Fang et al., "Three-dimensional cell cultures in drug discovery and development," Slas Discovery: Advancing Life Sciences R&D, Jun. 2017, 22(5):456-72.
Fiddler, "Fetal cell based prenatal diagnosis: perspectives on the present and future," Journal of Clinical Medicine, Sep. 2014, 3(3):972-85.
Fleming et al., "Colorectal carcinoma: Pathologic aspects," Journal of Gastrointestinal Oncology, Sep. 2012, 3(3):153-73.
Gerlinger et al., "Intratumor heterogeneity and branched evolution revealed by multiregion sequencing," New England Journal of Medicine, Mar. 8, 2012, 366:883-92.
Gracz et al., "A high-throughput platform for stem cell niche co-cultures and downstream gene expression analysis," Nature Cell Biology, Mar. 2015, 17(3):340-9.
Hsiao et al., "Microfluidic system for formation of PC-3 prostate cancer co-culture spheroids," Biomaterials, Jun. 1, 2009, 30(16):3020-7.
Ingram et al., "Three-dimensional growth patterns of various human tumor cell lines in simulated microgravity of a NASA bioreactor," In Vitro Cellular & Developmental Biology-Animal, Jun. 1997, 33(6):459-66.

Ishihara et al., "Mechano-signal transduction in mesenchymal stem cells induces prosaposin secretion to drive the proliferation of breast cancer cells," Cancer Research, Nov. 15, 2017, 77(22):6179-89.
Ivanov et al., "Spheroid arrays for high-throughput single-cell analysis of spatial patterns and biomarker expression in 3D," Scientific Reports, Jan. 30, 2017, 7(1), 13 pages.
Janiszewska et al., "The microcosmos of intratumor heterogeneity: The space-time of cancer evolution," Oncogene, Mar. 2020, 39(10):2031-9.
Kelm et al., "Method for generation of homogeneous multicellular tumor spheroids applicable to a wide variety of cell types," Biotechnology and Bioengineering, Jul. 20, 2003, 83(2):173-80.
Lee et al., "Isolation of spheroid-forming single cells from gastric cancer cell lines: enrichment of cancer stem-like cells," Biotechniques, Oct. 2018, 65(4):197-203.
Lelièvre et al., "Microphysiological systems to study microenvironment-cell nucleus interaction: importance of tissue geometry and heterogeneity," Microphysiological Systems, Dec. 2018, 2(12):10-21037.
Lin et al., "A microfluidic platform for high-throughput single-cell isolation and culture," Journal of visualized experiments: JoVE, Jun. 2016, (112), 7 pages.
Lindström et al., "Single-cell culture in microwells," Single-Cell Analysis 2012, 853, 41-52.
Liu et al., "Controllable organization and high throughput production of recoverable 3D tumors using pneumatic microfluidics," Lab on a Chip, 2015, 15(4):1195-204.
Maheswaran et al., "Ex vivo culture of CTCs: an emerging resource to guide cancer therapy," Cancer Research, Jun. 15, 2015, 75(12):2411-5.
Marusyk et al., "Intra-tumour heterogeneity: a looking glass for cancer?," Nature Reviews Cancer, May 2012, 12(5):323-34.
Meacham et al., "Tumour heterogeneity and cancer cell plasticity," Nature, Sep. 2013, 501(7467):328-37.
Mehta et al., "Opportunities and challenges for use of tumor spheroids as models to test drug delivery and efficacy," Journal of Controlled Release, Dec. 10, 2012, 164(2):192-204.
Paszek et al., "Tensional homeostasis and the malignant phenotype," Cancer Cell, Sep. 1, 2005, 8(3):241-54.
Qureshi-Baig et al., "What do we learn from spheroid culture systems? Insights from tumorspheres derived from primary colon cancer tissue," PloS one, Jan. 8, 2016, 11(1):e0146052, 24 pages.
Scher et al., "Phenotypic heterogeneity of circulating tumor cells informs clinical decisions between AR signaling inhibitors and taxanes in metastatic prostate cancer," Cancer Research, Oct. 15, 2017, 77(20):5687-98.
Schindelin et al., "Fiji: an open-source platform for biological-image analysis," Nature Methods, Jul. 2012. 9(7):676-82.
Schneider et al., "NIH Image to ImageJ: 25 years of image analysis," Nature Methods, Jul. 2012, 9(7):671-5.
Smart et al., "In vitro analysis of breast cancer cell line tumourspheres and primary human breast epithelia mammospheres demonstrates inter- and intrasphere heterogeneity," PloS one, Jun. 4, 2013, 8(6):e64388, 15 pages.
Souza et al., "Three-dimensional tissue culture based on magnetic cell levitation," Nature Nanotechnology, Apr. 2010, 5(4):291-6.
Tibbitt et al., "Hydrogels as extracellular matrix mimics for 3D cell culture," Biotechnology and Bioengineering, Jul. 1, 2009, 103(4):655-63.
Tirier et al., "Pheno-seq-linking visual features and gene expression in 3D cell culture systems," Scientific Reports, Aug. 26, 2019, 9(1):1-5.
Wang et al., "Cell adhesion and mechanical stimulation in the regulation of mesenchymal stem cell differentiation," Journal of Cellular and Molecular Medicine, Jul. 2013, 17(7):823-32.
Wang et al., "Cultured circulating tumor cells and their derived xenografts for personalized oncology," Asian Journal of Urology, Oct. 1, 2016, 3(4):240-53.
Weiswald et al., "Spherical cancer models in tumor biology," Neoplasia, Jan. 1, 2015, 17(1):1-5.
Yu et al., "Ex vivo culture of circulating breast tumor cells for individualized testing of drug susceptibility," Science, Jul. 11, 2014, 345(6193):216-20.

(56) References Cited

PUBLICATIONS

Zhang et al., "Micro RNA 100 sensitizes luminal A breast cancer cells to paclitaxel treatment in part by targeting mTOR," Oncotarget, Feb. 2, 2016, 7(5):5702-14.

Zhang et al., "Microfluidics 3D gel-island chip for single cell isolation and lineage-dependent drug responses study," Lab on a Chip, 2016, 16(13):2504-12.

Zhau et al., "Establishment of a three-dimensional human prostate organoid coculture under microgravity-simulated conditions: evaluation of androgen-induced growth and PSA expression," In Vitro Cellular & Developmental Biology—Animal, May 1, 1997, 33(5):375-80.

* cited by examiner

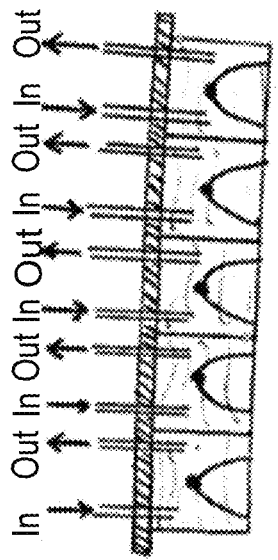
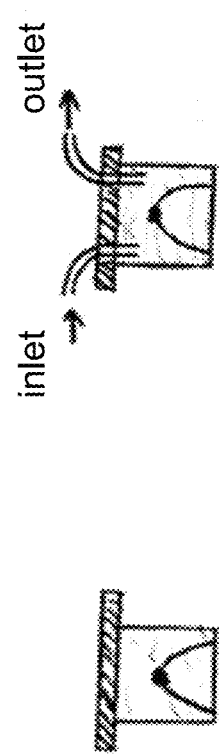
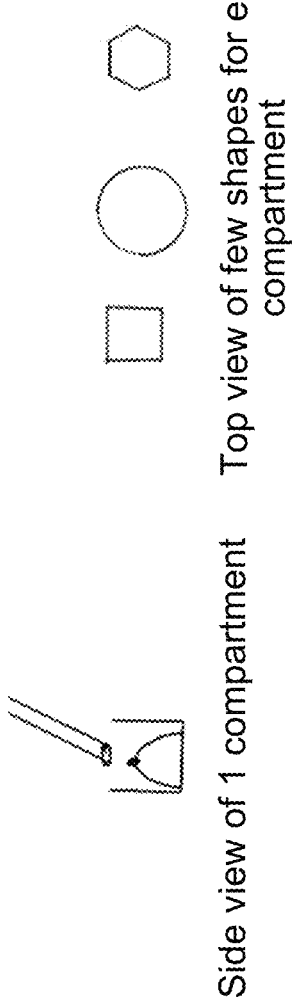
FIG. 2E
FIG. 2F

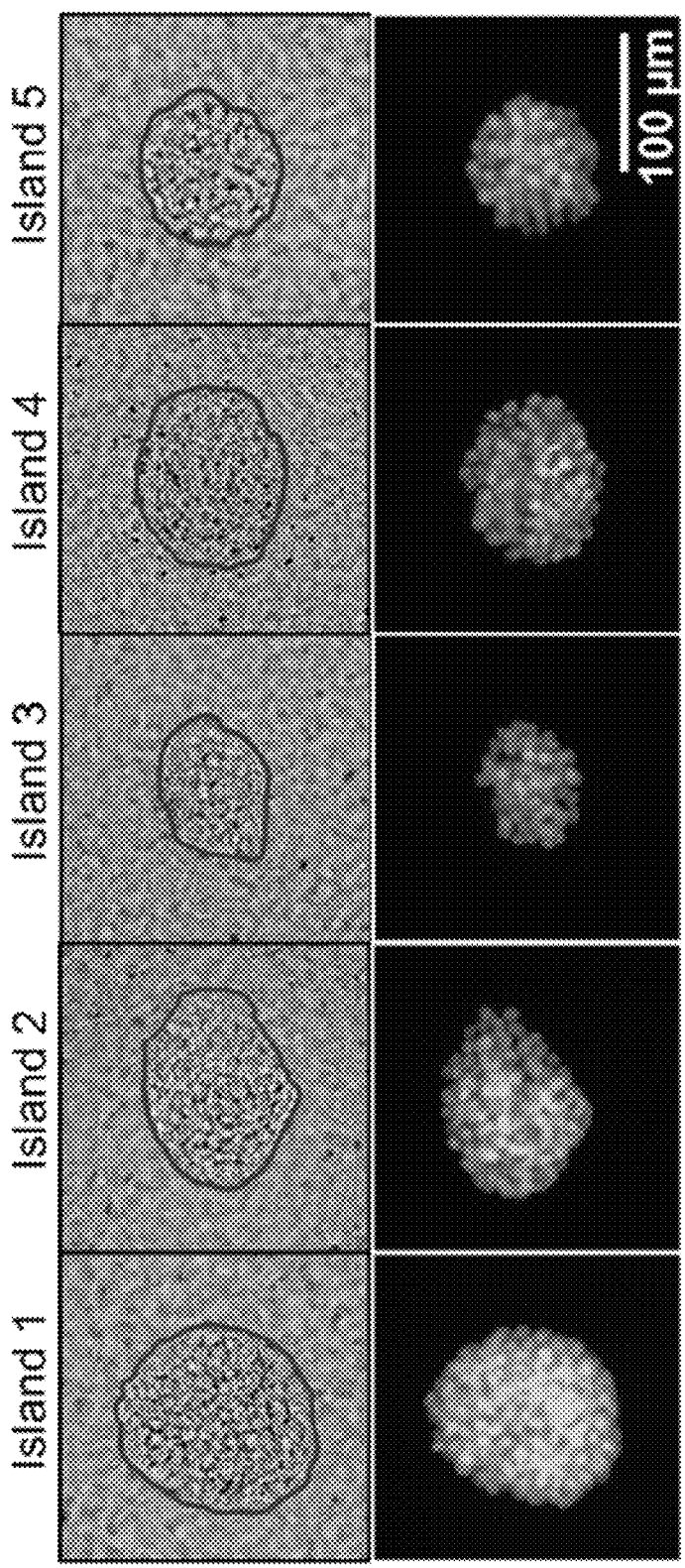

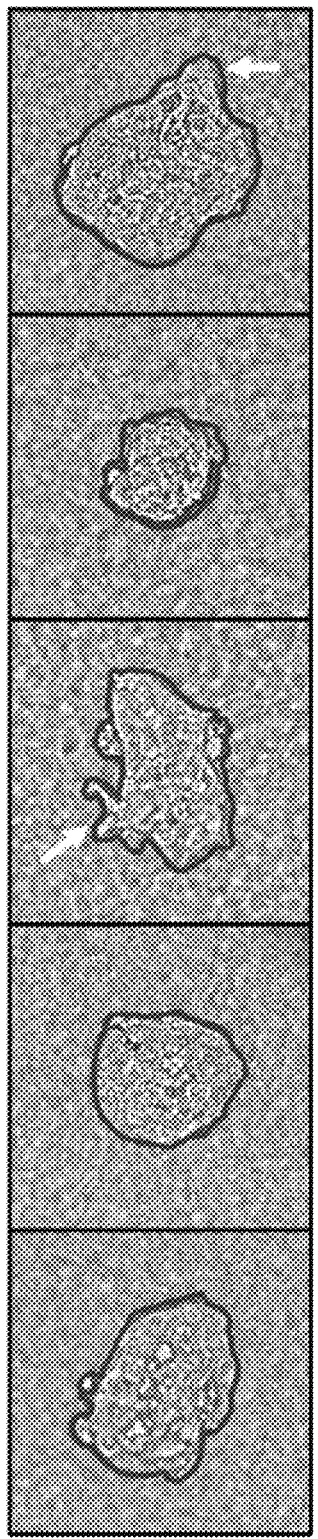
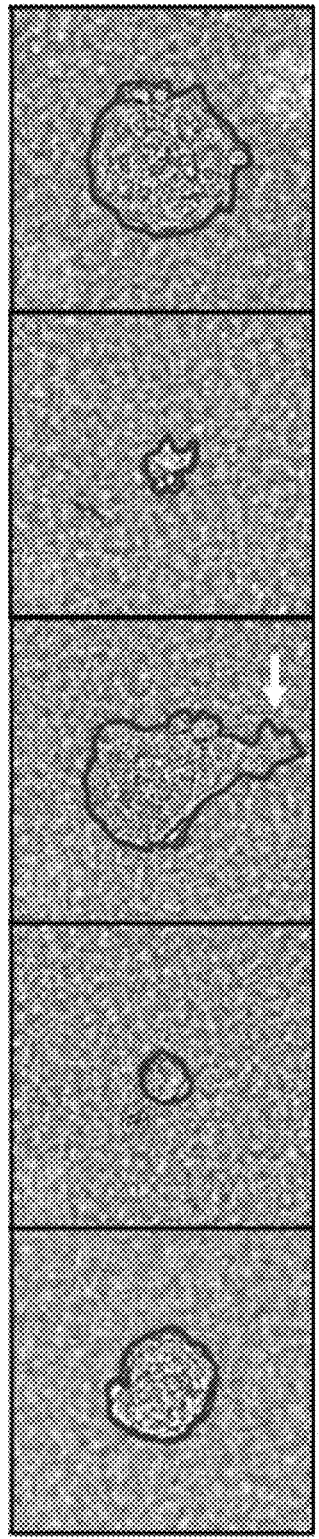
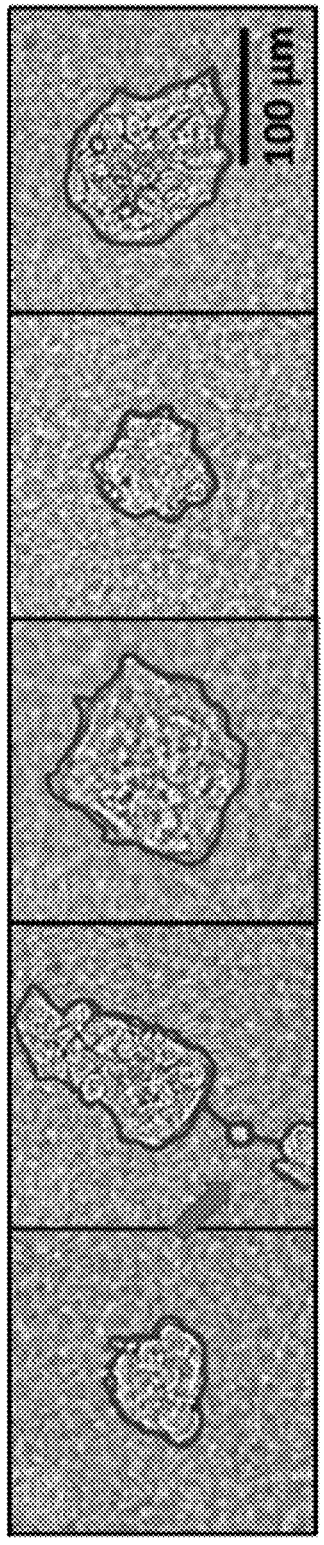

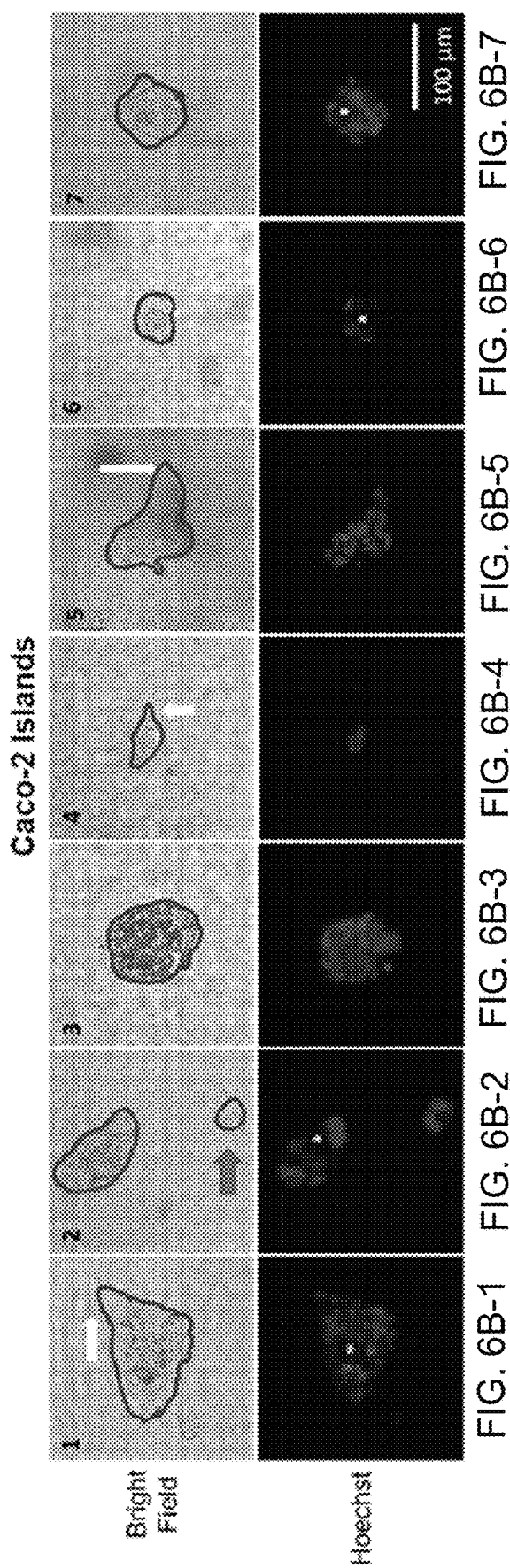

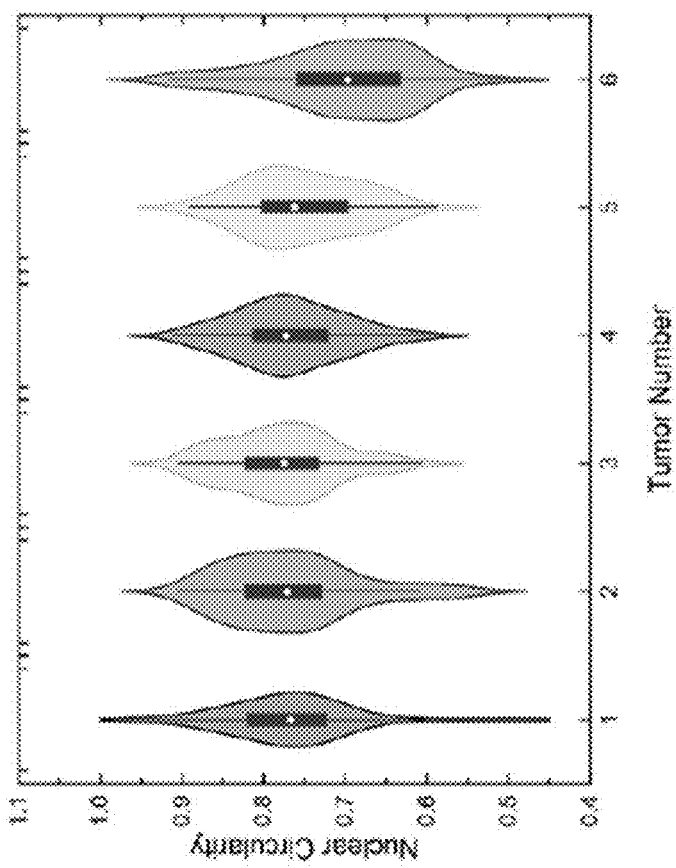
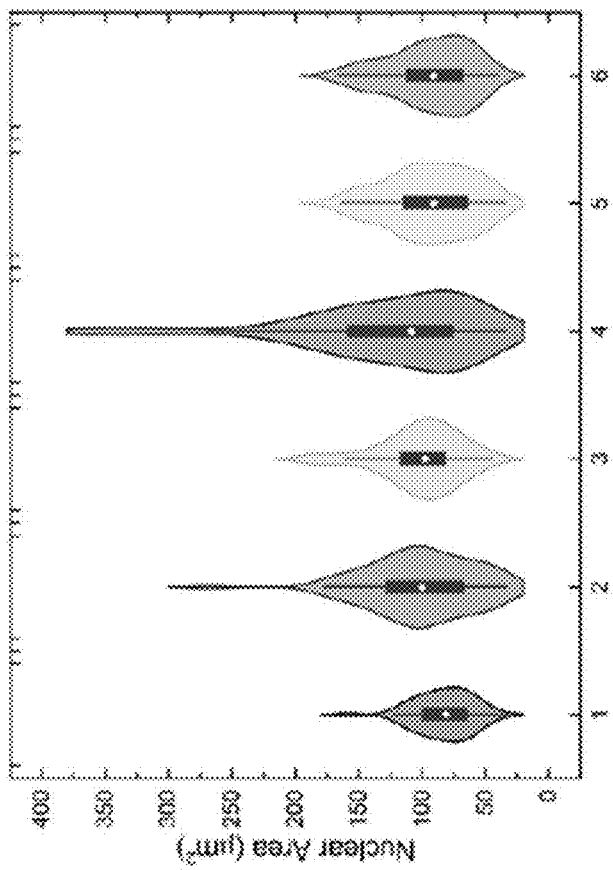
FIG. 7D
FIG. 7C

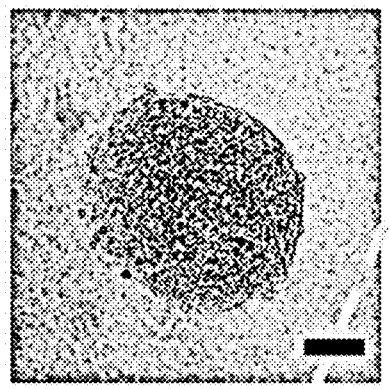
FIG. 9A-i
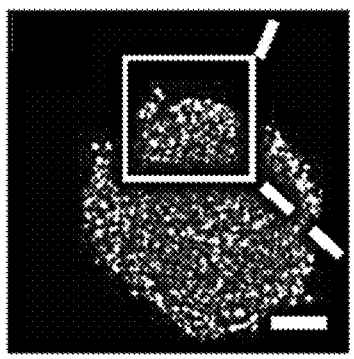
FIG. 9A-ii
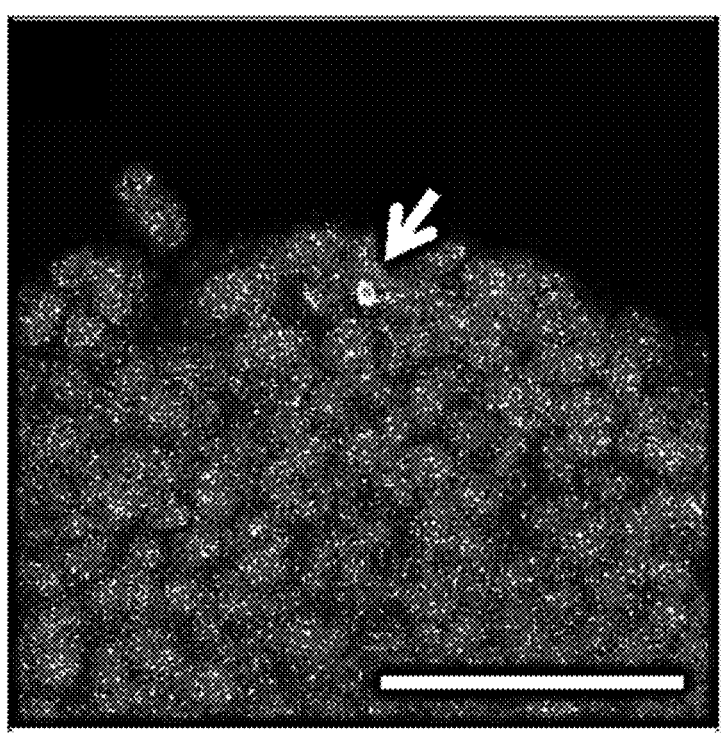
FIG. 9A-iii
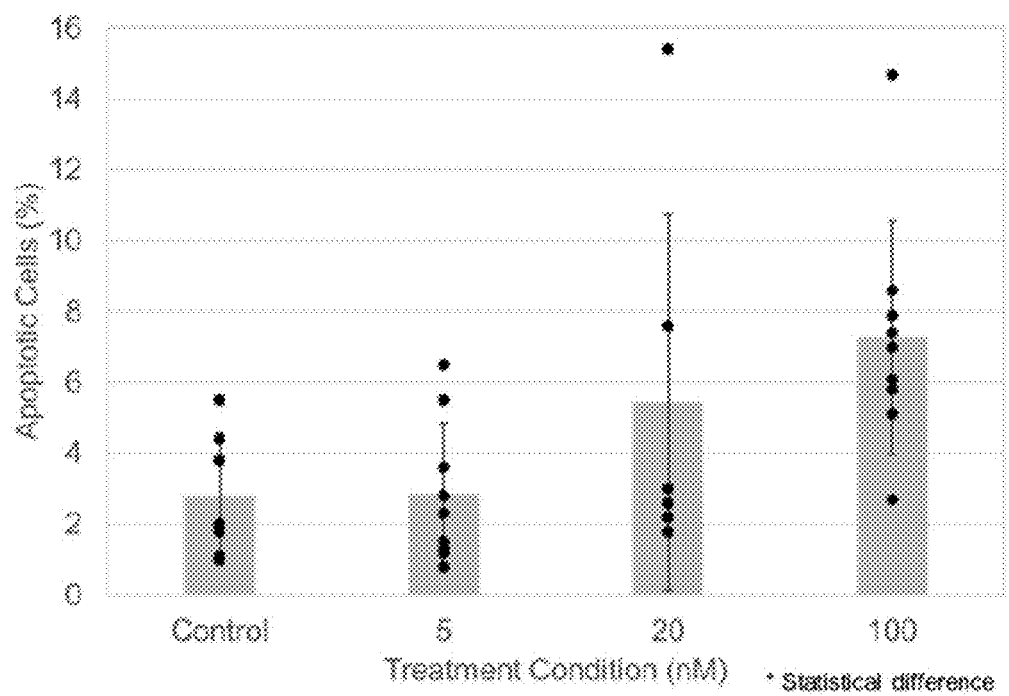
FIG. 9B

DETERMINISTIC CULTURING OF SINGLE CELLS

CLAIM OF PRIORITY

This application claims priority to U.S. Patent Application Ser. No. 63/036,060, filed on Jun. 8, 2020, the entire contents of which are hereby incorporated by reference.

FEDERALLY SPONSORED RESEARCH OR DEVELOPMENT

This invention was made with government support under grant number 1509097 awarded by the National Science Foundation. The government has certain rights in the invention.

TECHNICAL FIELD

The invention relates to methods and systems for culturing single cells and generating cell populations, e.g., tumors, starting from the single cell.

BACKGROUND

Three-dimensional (3D) cell culture methods are increasingly used to generate complex tissue models. Multicellular structures created by 3D cell culture should mimic aspects of in vivo microenvironments and generate organized cell assemblies that are biologically, histologically and molecularly more similar to in vivo conditions than standard 2D culture (see, e.g., Edmondson et al., *Assay Drug Dev. Technol.* 12, 207-18 2014). Such models developed with cancer cells also constitute an ideal platform for in vitro testing of therapeutic drugs (see, e.g., Edmondson et al., *Assay Drug Dev. Technol.* 12, 207-18 2014; and Fang et al., *Adv. life Sci. R D* 22, 456-472 2017). Cell lines and primary cells from patients' cancerous tissues have been successfully used in 3D cell cultures (see, e.g., Weiswald et al., *Neoplasia* 17, 1-15, 2015) to produce tumors.

Methods that employ non-adherent conditions can result in nonphysiologically-relevant cancer representations, which is exacerbated by the lack of progressive tumor development via cell division and the lack of interaction with an appropriate extracellular matrix (ECM). To address such issues, automated technologies to separate a large number of cells into single cells of interest, such as Fluorescence Activated Cell Sorting, have been employed to dispense single cells into microwells for culture (see, e.g., Lindstrom et al., *Methods Mol. Biol.* 853, 41 (2012). A limiting dilution method corresponding to the serial dilution of a suspension of cells has also been used to statistically (but not deterministically) contain one cell in a unit volume. This limiting dilution suspension is either mixed with an appropriate ECM or overlaid on top of it for cell culture (see, e.g., Tirier et al., *Sci. Rep.* 9, 2019; Qureshi-Baig et al., *PLoS One* 11, 2016; and Lee et al., *Biotechniques* 65, 197-203, 2018). While these methods are valid to obtain single cells from a large population of cells, they are impractical when the cell population is small as they generate considerable cell loss during mixing and/or transfer.

Microfluidic platforms have been developed to for single cell culture in 3D (see, e.g., Chen et al., *Lab Chip* 16, 2935-2945, 2016; Cheng et al., *Lab Chip,* 16, 3708-3717, 2016; Lin et al., *J Vis. Exp.* 2016, 2016; Gracz et al., "A high-throughput platform for stem cell niche co-cultures and downstream gene expression analysis," doi:10.1038/ncb3104; and Zhang et al., *Microfluidics,* "3D gel-island chip for single cell isolation and lineage-dependent drug responses study," 16, 2014). However, in these methods, all cells in the original suspension are eventually cultured without discrimination.

Accordingly, there exists a need in the art for methods and systems for deterministic selecting and culturing of single cells.

SUMMARY

The disclosure relates to methods and systems for culturing individual cells, e.g., individually selected cells, in relative isolation from the rest of a population of cells, under physiologically relevant and controllable environmental conditions that can be designed to mimic specific environments, e.g., an environment within a human body. For example, the new methods and systems can be used to select a specific single cell from a cell population, e.g., based upon cellular biomarkers, size, etc., to form a pure tissue, e.g., a pure tumor, of all the same type of cells. The environment can be carefully controlled to mimic a specific in vivo micro-environmental condition, such as stiffness of a supporting matrix, pH, lymph, blood, growth factors, chemokines, other supporting cells, etc., to provide controlled culturing conditions ex vivo. Thus, the tissue can be grown in conditions mimicking, for example, bone marrow, ducts within breast tissue, neurological tissue, and the like.

Accordingly, provided herein are methods for deterministically culturing a single cell, the method comprising: (a) providing a three-dimensional culturing island comprising a matrix attached to a surface of a culture vessel and in contact with a culture medium, wherein one or more parameters of each of the matrix and the culture medium are selected by the user, based on one or more micro-environment selection criteria; (b) selecting a single cell from a population of cells using one or more cell selection criteria; (c) seeding the single selected cell onto or into the culturing island and providing a time sufficient to enable the single cell to adhere to a surface of the culturing island or adhere to the matrix within the culturing island; (d) adding additional culture medium in an amount sufficient to submerge the seeded single cell and the culturing island in the culture medium; and (e) culturing the single cell on or within the culturing island for a time and under conditions sufficient to grow a multi-cell tissue from the single cell.

In some embodiments, the matrix is selected from the group consisting of collagen, Matrigel® (a gelatinous protein mixture that resembles extracellular matrix used for culturing cells), elastin, and laminin-based extra cellular matrices. In some embodiments, the matrix is cross-linked.

In some embodiments, a plurality of culturing islands are attached to the surface of the culture vessel, wherein each culturing island is separated and not in contact with any other culturing island. In some embodiments, a distance between the culturing islands is at least about 1 mm. In some embodiments, the culturing islands are separated in individual compartments. In some embodiments, the volume of the culturing island(s) is about 0.1 µl to about 1 ml. In some embodiments, the diameter of the culturing island is about 1 mm to about 10 mm.

In some embodiments, the methods further include or consist of stiffening the culturing island(s).

In certain embodiments, the surface of the culture vessel is an inner surface of a tissue culture dish.

In some embodiments, the seeding in step (c) includes positioning the single cell on the top of the culturing island.

In other embodiments, the seeding in step (c) includes embedding the single cell in the culturing island. In certain embodiments, the seeding in step (c) includes positioning a first single cell on the top of a first culturing island and embedding a second single cell in a second culturing island on the same surface.

In some embodiments of any one of the methods described herein, the method further includes separating a plurality of cells into single cells prior to step (b). In some embodiments, separating the plurality of cells includes physical disruption of the plurality of cells or trypsinizing the plurality of cells.

In some embodiments, the one or more microenvironments is a cancer microenvironment.

In some embodiments, the single selected cell is selected using a microfluidic device and/or the single selected cell can be seeded using a microfluidic device. In some embodiments, the microfluidic device includes a hollow capillary tube with an inner diameter of about 5 μm to about 5 mm.

In some embodiments, the culture medium is a biological fluid or a liquid extracted from particular tissues or glands. In certain embodiments, the culture medium is selected from blood, plasma, and lymph fluid. In other embodiments, the culture medium is an artificial medium selected from a balanced salt solution or a complex medium.

In some embodiments, the single cell on the culturing island is cultured for about 8 to about 11 days. In certain embodiments, the population of cells in step (b) comprises about 1 to about 10,000 cells.

In some embodiments, the single cell is a single tumor cell, or the multi-cell tissue is a tumor tissue. For example, the tumors can be colorectal tumors or breast tumors. In some embodiments, a single tumor cell is isolated from a patient.

In some embodiments, the methods further include retrieving the tumor from the culturing island.

In certain embodiments of the any one of the methods described herein, the methods further include separating the cells in the tumor into single cells and re-culturing the single cells.

In some embodiments, the one or more cell selection criteria are the expression level of one or more cell-surface molecules, the morphology of the cell, shape of the cell, circularity and aspect ratio of the cell, stemness of the cell, e.g., the level of one or more parameters that indicate the cell is a stem cell rather than an ordinary cell, proliferation potential of the cell, type of the cell, morphology of the nucleus, presence of nuclear foci, genetic composition, epigenetic modifications, and/or the secretion of one or more cytokine or chemokine by the cell.

In some embodiments, the methods further include or consist of administering the therapeutic agent to the multi-cell tissue in step (e), thereby testing the therapeutic agent.

In some embodiments, the methods further include or consist of administering one or more therapeutic agents to the multi-cell tissue in step (e), thereby screening for a therapeutic agent.

In another aspect, the present disclosure features systems for deterministically culturing a single cell. The systems include or consist of a culture vessel for housing a three-dimensional culturing island including a matrix attached to a surface of the culture vessel and in contact with a culture medium, wherein one or more parameters of each of the matrix and the culture medium are selected by the user, based on one or more micro-environment selection criteria; a cell picking system including a visualization system, e.g., a microscope, and a single cell retrieval device, e.g., a micropipette and suction or vacuum system, arranged for selecting a single cell from a population of cells using one or more cell selection criteria; a robotic system for supporting and controlling the single cell retrieval device to retrieve and seed the single selected cell onto the culturing island; optionally a culture medium distribution system, to apply culture medium in an amount sufficient to submerge the seeded single cell and the culturing island in the culture medium; and further optionally a control system for automatically controlling the cell picking system, single cell retrieval device, and robotic system for automatically selecting a single cell according to the selection criteria, e.g., programmed cell selection criteria, and automatically seeding the single cell on the culturing island, e.g., produced according to micro-environment selection criteria, e.g., programmed micro-environment selection criteria, and to control culturing conditions, e.g., automatically, for a time sufficient to grow a multi-cell tissue from the single cell.

As used herein, the phrases "deterministic culturing" or "deterministically culturing" mean a culture technique in which a user selects a specific single cell based on one or more cell selection criteria, and once that single cell is selected and cultured, its progeny in culture are determined precisely, without any random chance involved, as opposed to, for example, stochastic culturing methods, in which cells are selected at random from a population of cells and then cultured, e.g., based on a random probability distribution or pattern, which can be analyzed statistically, but cannot be predicted precisely.

As used herein, a "three-dimensional culturing island" or "culturing island" means a structure having a height, a depth, and a width that serves as a scaffold to provide support for a single cell to attach, grow, and/or proliferate. A culturing island can comprise a matrix that is made of a natural or synthetic material.

As used herein, a "microenvironment" means the immediate small-scale environment of a cell culture or a part of a cell culture, especially as a distinct part of a larger environment, e.g., within a culture vessel. The microenvironment of a tumor is an integral part of its physiology, structure, and function. It is an essential part of the tumor, because it supplies a nurturing condition for the malignant process.

As used herein, a "seed" means a cell that initiates a culturing process. A seed can be a single cell or a collection of cells. Preferably, a seed is a single cell. As used herein, "seeding" means the process of initiating a cell culture.

The new methods and systems can be used to study phenotypic heterogeneity of tumors, to study aggressiveness of different tumor cells and types of cells, and/or to test multiple different drugs on tissues, e.g., tumor tissues, all made from different types of starting cells in the same or different micro-environments. The new methods and systems are especially useful when analyzing rare cells, such as circulating tumor cells (CTCs), stem cells, fetal cells, subpopulations of immune cells, T or B cells, as well as CAR-T cells.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 2E is a series of schematic diagrams that show side and top views of different types and shapes of compartments for individual culturing islands within a culture vessel.

FIG. 2F is a series of schematic diagrams that show separate inlets and outlets for individual compartments in a culture vessel housing multiple compartments.

FIGS. 4A-4E are a series of microscope images that show tumors developed from single MCF-7 cells, visualized using bright-field microscopy (top) as well as Hoechst-based fluorescence microscopy (bottom) after 10 days of culture (tumors are outlined using Microsoft EXCEL).

FIGS. 6A-i to 6A-xv are a series of bright-field microscope images of MCF-7 tumors; short 'arm-like' structures are indicated by white arrows in iii, v, and viii.

FIGS. 6B-1 to 6B-7 are a series of bright-field and Hoechst fluorescence microscope images of Caco-2 tumors; the angular shape of certain tumors is indicated by thick white arrows (1, 4, and 5). Apparent central hollowness of tumors in islands 1, 2, 6, and 7 that are characteristic of glandular-like adenocarcinoma are indicated by an asterisk in the Hoechst images. Secondary tumor formation possibly linked to cell migration is visible on one image of each set of images for MCF7 (see FIG. 6A-xii) and Caco-2 (FIG. 6B-2) tumors, as shown by dark arrows.

FIGS. 7C-7D are violin plots of nuclear area and circularity for each of the six tumors where fifty to 75 nuclei were analyzed per tumor.

FIGS. 9A-i to 9A-iii are a series of bright-field and fluorescent microscope image that shows the results of treatment of MCF7 tumors with paclitaxel. Single MCF7 cells were cultured on collagen islands for 13 days before treatment with paclitaxel or vehicle DMSO (Control) for 24 hours. FIGS. 9A-i and ii show bright-field and confocal fluorescence (Hoechst) images of a tumor after treatment with 5 nM of paclitaxel. iii Zoomed portion of image ii showing nuclei with one apoptotic (smaller and brighter) nucleus (white arrow). Scale bar: 100 µm.

FIG. 9B is a bar graph of the percentage of apoptotic cells. Black dots represent individual tumors and black vertical lines represent standard deviations. Two-tailed heteroscedastic t-test based P-values for each of the six pairs of treatment are as follows: DMSO with 5 nM-0.972, DMSO with 20 nM-0.291, DMSO with 100 nM-0.004, 5 nM with 20 nM-0.297, 5 nM with 100 nM-0.004, 20 nM with 100 nM-0.477.

DETAILED DESCRIPTION

Figure 1:
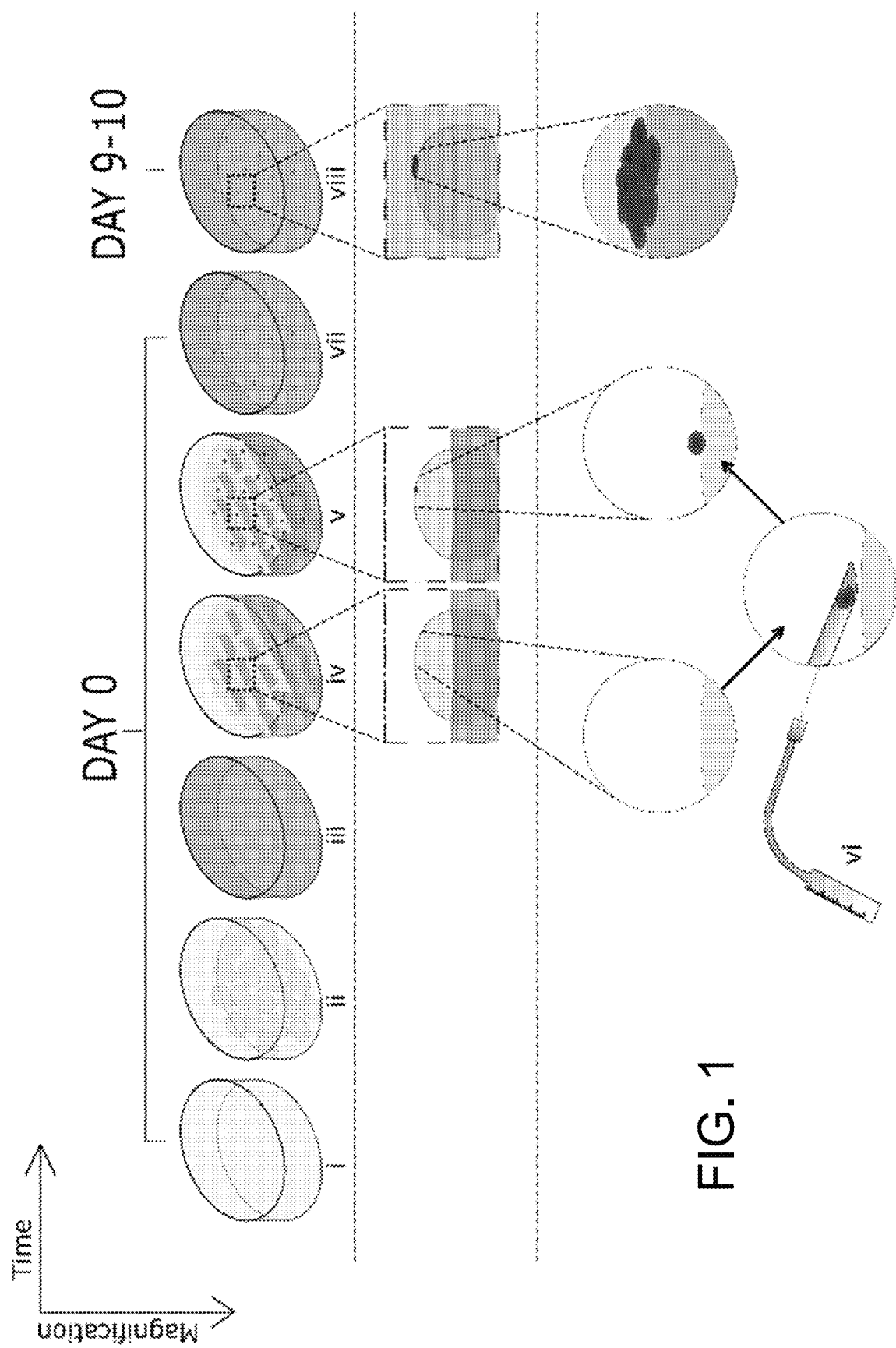
FIG. 1 is a schematic illustration of an example of a workflow of deterministic single cell culturing as described herein.

The disclosure relates to methods and systems for culturing individually selected cells in relative isolation from the rest of a population of cells, under physiologically relevant and controllable environmental conditions that can be designed to mimic specific environments, e.g., within a human body.

The methods and systems use a deterministically targeted single cell as the seed. Only a chosen single cell is individually positioned on top of or within a collagen island. For example, a specific single cell from a cell population is selected, e.g., based upon cellular biomarkers, size, etc., to form a pure tissue, e.g., a pure tumor, of all the same type of cells. The environment can be carefully controlled to mimic specific in vivo micro-environmental conditions, such as stiffness of a supporting matrix, pH, lymph, blood, growth factors, chemokines, other supporting cells, etc., to provide controlled culturing conditions in an ex vivo setting. Thus, the tissue can be grown in conditions mimicking, for example, bone marrow, ducts within breast tissue, neurological tissue, and the like.

Furthermore, the tissues, e.g., tumors generated using the methods and systems can be easily extracted from their culture location and transferred elsewhere for long-term culture or subsequent downstream analyses, for example, screening and testing of therapeutic agents (e.g., anti-tumor agents).

The methods and systems are highly useful for a range of applications, including propagating extremely rare cells (like circulating tumor cells (CTCs) and circulating fetal cells), as well as studying the nature and impact of phenotypic heterogeneity in tumors and tissues. The deterministic aspect of the culture method can be developed via imaging of epigenetic modifications to select cells with different epigenetic make-up and follow the resulting tissue formation at registered locations under defined 3D cell culture conditions.

Methods of Deterministic Culturing of Selected Single Cells

Provided herein are methods for deterministically culturing a single cell, the methods include (a) providing a three-dimensional culturing island having a matrix attached to a surface, e.g., a bottom surface, of a culture vessel and in contact with a culture medium; wherein one or more parameters of each of the matrix and the culture medium are selected by the user, based on one or more micro-environment selection criteria such as chemical composition, stiffness, pH, porosity, presence of specific molecules that facilitate cell attachment, probe cell proliferation or cause cells (e.g. stem cells) to differentiate into organ-specific cells; b) selecting a single cell from a population of cells using one or more cell selection criteria such as surface markers, protein expression pattern, nuclear morphology, cellular morphology, genetic composition, epigenetic modifications, size, circularity, aspect ratio, cell type, degree of stemness; (c) seeding the single selected cell onto or into the culturing island and providing time sufficient to enable the single cell to become adhered to a surface or interior of the culturing island; (d) adding additional culture medium in an amount sufficient to submerge the seeded single cell and the culturing island in the culture medium; and (e) culturing the single cell on the culturing island for a time and under conditions sufficient to grow a multi-cell tissue from the single cell.

Culturing times can vary greatly depending on the type of cell being cultured. For instance, breast cancer cell line MCF-7 can take up to 7 days to form multicellular tumors. At some point in time, the tumors become too big and start developing a necrotic core. These times can range from few days to few months depending on the cell type being used.

The single selected cell can be cultured for any suitable duration that is sufficient to grow a multi-cell tissue. In some embodiments, the single selected cell is cultured for about 1 day to about 21 days (e.g., about 1 day to about 5 day, about 5 day to about 10 day, about 10 days to about 15 days, about 15 day to about 21 day). In some embodiments, the single selected cell is cultured for about 8 day to about 10 days. In some embodiments, the culture medium is changed, e.g., replaced with the same or a different amount of the same or a different medium, about every 5-7 days. In some embodiments, the culture medium is changed, e.g., replaced with the same or a different amount of same or a different medium, about every 2-3 days.

Typical environmental conditions for culturing of most human cell lines involve maintaining the temperature at 37° C. (plus or minus 1-2° C.), humidity at 95% and $CO_2$ concentration at 5%. Other suitable culturing conditions can also be used in the methods described herein. Culture medium may include several components including balanced salt solutions, carbon sources, amino acids, vitamins, phenol dyes, buffers, and a variety of growth factors such as fibroblast growth factor (FGF), epidermal growth factor (EGF), and pleteletdericed growth factor (PDGF).

FIG. 1 is an example of a workflow of the method for deterministically culturing of a single cell. Specifically, on Day 0, a tissue culture dish (i) is provided and three-dimensional culturing islands are attached to the inner surface of the culture dish (ii). Culture medium is added to the dish (iii) while the top of each culturing island is not submerged in the culture medium (iv). A single cell is selected and picked and positioned on the top of each culturing island (v) using a device including a glass capillary (vi). Additional culture medium is then added to the dish in an amount sufficient to submerge the seeded single cell and the culturing island in the culture (vii). The seeded single cells are then cultured for about 9 to about 10 days to allow the cells to grow and proliferate into a multi-cell tissue (viii).

The three-dimensional culturing islands described herein can be in any suitable shape or form that supports the attachment and proliferation of the single cell. In some embodiments, the culturing island is in a solid form. In some embodiments, the culturing island is in a semi-solid form. In some embodiments, the methods described herein further comprises stiffening the culturing island.

The diameter of the three-dimensional culturing island is a function of volume of matrix used and its viscosity and stiffness. In some embodiments, the diameter of the three-dimensional culturing island is about 0.5 mm to about 15 mm. In some embodiments, the diameter of the three-dimensional culturing island is about 1 mm to about 10 mm. In some embodiments, the diameter of the three-dimensional culturing island is about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. The diameter of the three-dimensional culturing island can also be of any suitable value for single cell culturing.

The volume of the three-dimensional culturing islands can be any suitable volume that allows the attachment (or insertion) and proliferation of a single cell. The volume of the culturing islands can be adjusted based on, for example, the surface area or type of the culture vessel. In some embodiments, the volume of the three-dimensional culturing island is about 0.1 µl to about 1 ml. In some embodiments, and preferably, the volume of the three-dimensional culturing island is about 0.1 µl to about 100 µl. In some embodiments, the volume of the three-dimensional culturing island is about 0.1 µl to about 10 µl. In some embodiments, the volume of the three-dimensional culturing island is about 0.1 µl to about 1 µl. In some embodiments, the volume of the three-dimensional culturing island is about 1 µl to about 10 µl. In some embodiments, the volume of the three-dimensional culturing island is about 1 µl to about 100 µl. In some embodiments, the volume of the three-dimensional culturing island is about 1 µl to about 1 ml. In some embodiments, the volume of the three-dimensional culturing island is about 10 µl to about 100 µl. In some embodiments, the volume of the three-dimensional culturing island is about 10 µl to about 1 ml.

Figure 2A:
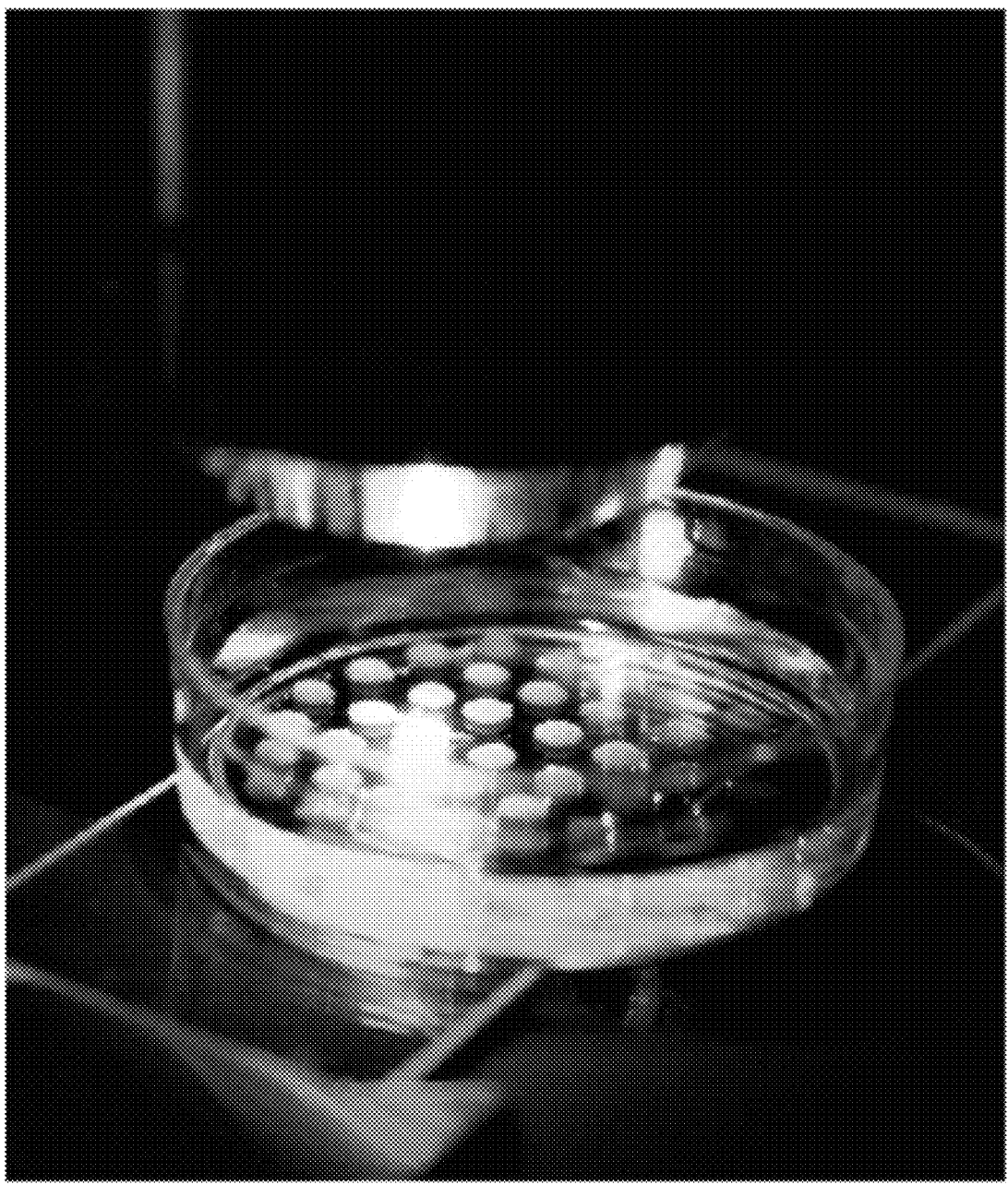
FIG. 2A is a representation of a photographic image of hemispherical islands (n=40) of collagen I matrix on a polystyrene culture dish, where each island receives exactly one single cell for culture.

In some embodiments, a plurality of three-dimensional culturing islands are attached to the surface of the culture vessel, wherein each culturing island is separated and not in contact with any other culturing island. An example of a plurality of culturing islands attached to the surface of the culture vessel is shown in FIG. 2A.

In some embodiments, about 1 to about 1000 (about 1 to about 1000, about 1 to about 100, about 1 to about 10, about 10 to about 1000, about 10 to about 100, or about 100 to about 1000) three-dimensional culturing islands are attached to the surface of the culture vessel.

A distance between any two culturing islands should be big enough so that an individual single cell can be seeded onto a culturing island and proliferate without interfering with the single cell on any other culturing island in the same culture vessel. In some embodiments, the center to center distance between the culturing islands is at least about 1, about 2, about 3, about 4, about 5, about 6, about 7, about 8, about 9, or about 10 mm. In some embodiments, a distance between the culturing islands is at least about 0.5 mm. In some embodiments, a distance between the culturing islands is about 0.5 mm, about 1 mm, about 2 mm, about 3 mm, about 4 mm, about 5 mm, about 6 mm, about 7 mm, about 8 mm, about 9 mm, or about 10 mm.

In some embodiments, culturing islands are attached to the surface of the culture vessel in an ordered format so that each island can be identified by position or location and/or with an index.

The culture vessel used in the methods described herein can be any suitable culture vessel. For example, the culture vessel can be a tissue culture dish, e.g., a 35 mm culture dish, a 10 cm dish, a 6-well culture plate, a 12-well culture plate, a 24-well culture plate, a 48-well culture plate, or a 96-well culture plate. In some embodiments, the three-dimensional culturing islands are attached to the inner surface of the culture vessel.

Figure 2B:
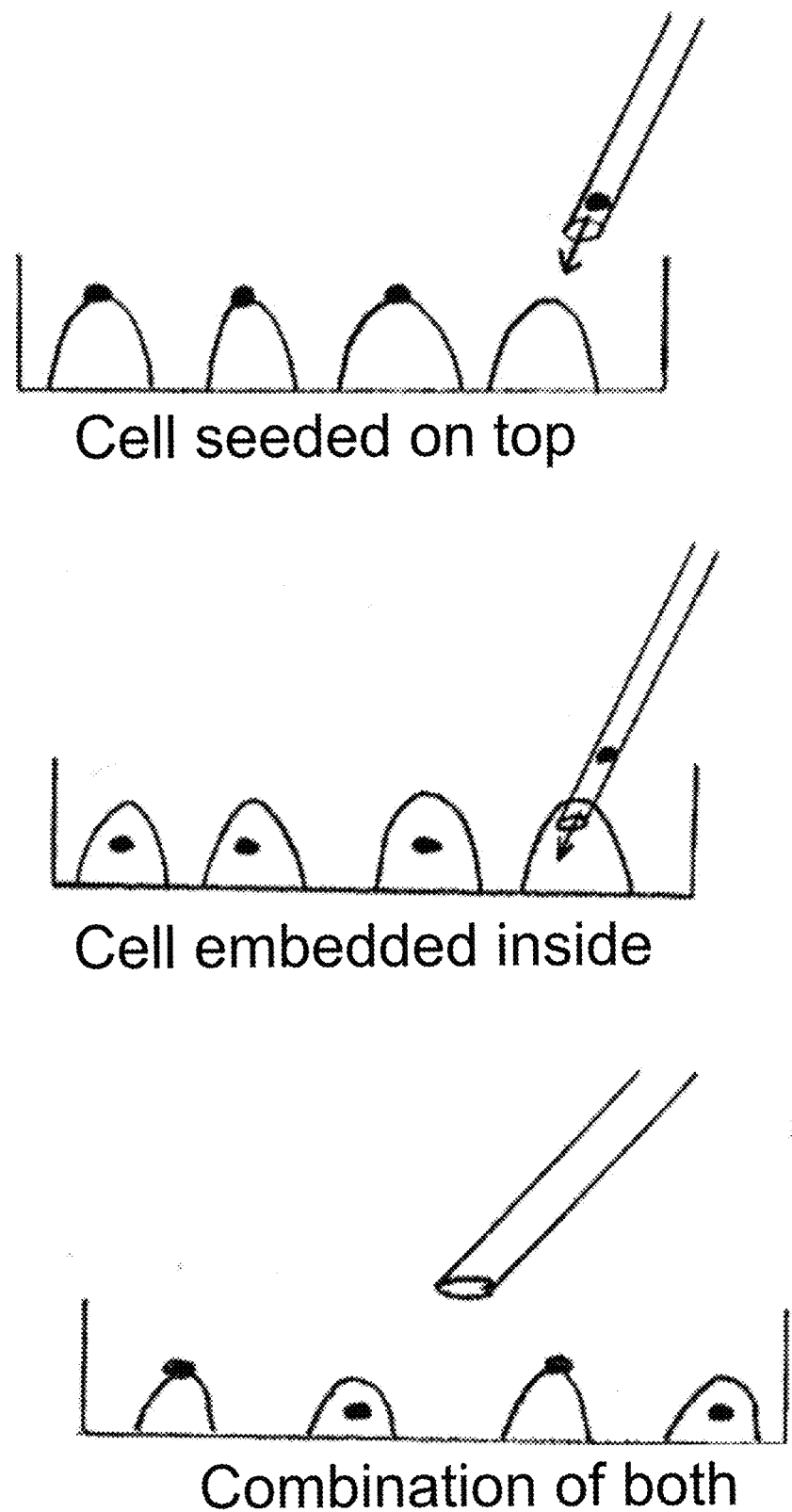
FIG. 2B is a series of schematic diagrams of the positioning of single cells on or within culturing islands, or a combination of both on and within culturing islands.

As shown in FIG. 2B, the single selected cell can be seeded onto or into the culturing island in any suitable way. In some embodiments, seeding the cell involves positioning the single cell on the top of the culturing island. In some embodiments, seeding involves embedding the single cell in the culturing island. In some embodiments, the seeding involves positioning a first single cell on the top of a first culturing island and embedding a second single cell in a second culturing island on the same surface.

Figure 2C:
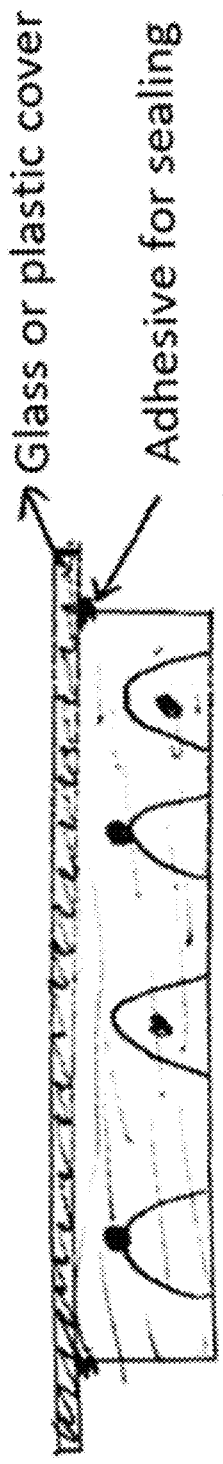
FIG. 2C is a schematic diagram of a culture vessel as described herein having a cover, e.g., a glass or plastic cover.
Figure 2D:
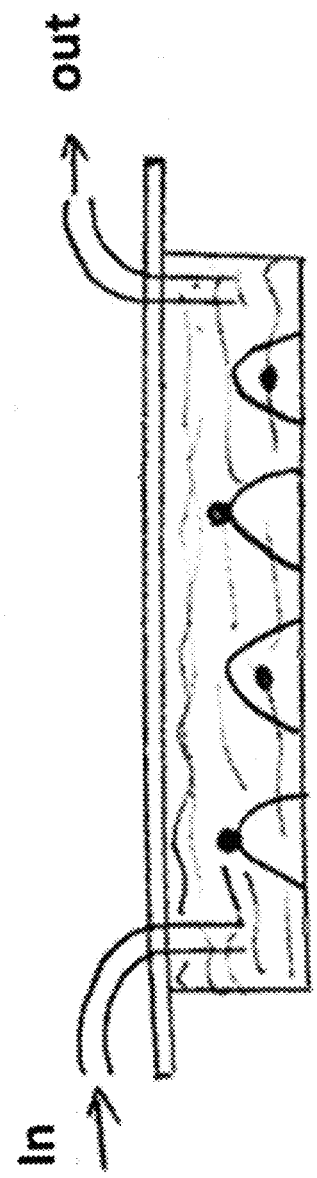
FIG. 2D is a schematic diagram of a culture vessel as described herein having a cover and inlets and outlets for exchange of fluids.

As shown in FIG. 2C, the culture vessel, e.g., culture dish may be sealed with a glass or plastic cover for long term storage and imaging. As shown in FIG. 2D, a sealed culture vessel, e.g., culture dish, may be provided with one or more inlet and outlets for exchange of fluids during or after the culture period. These inlets and outlets may be fitted with appropriate adapters and tubing for connection to a pump for better control of the flow rate. They may also be used manually by connecting to a syringe.

In some embodiments, a plurality of three-dimensional culturing islands are separated in individual compartments. Any suitable compartments can be used to separate the culturing islands. For example, as shown in FIGS. 2E-2F, a cell culture dish that may have individual compartments for accommodating exactly one island and one cell on top of or inside it for cell culture can be used as described herein. The size of each compartment will be at least equal to the volume of the island and may have different shapes. Each compartment may also be sealed, e.g., using a glass cover, and may have inlets and outlets for handling of liquid in individual compartments. In some embodiments, each compartment is isolated from the other compartments. In some embodiments, compartments do not share fluids such as culture medium. In some embodiments, compartments are individually sealed.

The matrix in the culturing island can be any suitable matrix for culturing a cell. The matrix can be natural or synthetic. In some embodiments, the matrix is an extracellular matrix. In some embodiments, the matrix comprises one or more component of an extracellular matrix, such as collagen, Matrigel®, fibronectin, elastin, laminin, laminin-based extra cellular matrices, hyaluronic acid, heparin, chondroitin, and/or keratin. In some embodiments, the matrix comprises Matrigel®.

In some embodiments, the matrix is made of a cross-linked material. Heat, light, or chemical reagents may be used to crosslink and solidify the matrix into desired shape on the surface of the culture vessel. The stiffness of the extra cellular matrix used can be representative of different stiffness of human body tissue, which varies between about 50 Pa (e.g., for soft tissue such as brain) to greater than 100 kPa (e.g., for bone tissue).

Deterministic culturing allows for differential treatment of cells of interest even when they are from the same population. This is difficult to achieve with other methods that do not allow for individual treatment of cells. Thus, selected cells from the same sample, e.g., circulating tumor cells (CTCs) from a blood sample, can be seeded on different culturing islands in the same culture vessel. Deterministic culturing protocol allows for choosing different soil and culture conditions for the single selected cells from the same sample because each cell is treated individually.

In some embodiments, one or more parameters of each of the matrix and the culture medium are selected by the user based on one or more micro-environment selection criteria.

In some embodiments, the parameters of the matrix are selected based on a specific micro-environment. For example, a subgroup of cells from a blood sample can be seeded in extra-cellular conditions that are similar to brain while other cells from the same sample may be seeded in extra-cellular conditions similar to lung, liver, or bone. In some embodiments, the microenvironment is a cancer microenvironment.

In general, the parameters of the culture medium are selected to achieve a specified micro-environment. For example, single cells are seeded in different culture dishes and supplied with culture media having different compositions. Different culture vessels can also be supplied with different biochemical factors that affect proliferation and/or differentiation of cells.

Single cells are selected from a population of cells using one or more criteria. These criteria include, but are not limited to, the expression level(s) of cell-surface markers, e.g., cancer antigens, the morphology of the cells, size of the cells, shape of the cells, aspect ratio and circularity of the cells, the type of cells, the invasiveness and proliferation potential of cells, stemness of cells, protein expression pattern, nuclear morphology (such as size or circularity), cellular morphology, presence of nuclear foci, genetic composition, epigenetic modifications, size, circularity, aspect ratio, cell type, degree of stemness, and the secretion of one or more cytokines or chemokine by the cells. In some embodiments, the population of cells comprises about 1 to about 10,000 cells. In some embodiments, the single selected cell is selected using a microfluidic device.

The single selected cell can be any suitable cell. In some embodiments, the single selected cell is a single tumor cell. In some embodiments, the single tumor cell is selected from a tumor tissue. In some embodiments, the single tumor cell is a circulating tumor cell (CTC) selected from a bodily fluid (e.g., blood or lymph).

The single selected cell can be seeded by any suitable methods. In some embodiments, the single selected cell is seeded using a microfluidic device. In some embodiments, the single selected cell is seeded using a syringe.

After the single selected cell is seeded onto the culturing island, sufficient time is provided to enable the single cell to adhere to a surface of the culturing island. In some embodiments, about 10 minutes to about 60 minutes (about 10 minutes to about 50 minutes, about 10 minutes to about 40 minutes about 10 minutes to about 30 minutes about 10 minutes to about 20 minutes, about 20 minutes to about 60 minutes, about 20 minutes to about 50 minutes, about 20 minutes to about 40 minutes about 20 minutes to about 30 minutes) are provided to enable the single cell to adhere to a surface of the culturing island.

In some embodiments, the top of the three-dimensional culturing islands is not submerged in the culture medium prior to the seeding of the single selected cell. In some embodiments, the methods include adding additional culture medium in an amount sufficient to submerge the seeded single cell and the culturing island in the culture medium.

The methods described herein provide culturing the single cell on the culturing island for a time and under conditions sufficient to grow a multi-cell tissue from the single cell. In some embodiments, the single cell is cultured under a normoxia condition. In some embodiments, the cell is cultured under 37° C. temperature, 5% $CO_2$ concentration and 95% Relative Humidity. In some embodiments, the cell is cultured under a hypoxic condition.

In some embodiments, the methods described herein further comprises separating a plurality of cells into single cells prior to (b) selecting a single cell from a population of cells using one or more cell selection criteria. In some embodiments, separating the plurality of cells comprises physical disruption of the plurality of cells, e.g., aspiration of cells. In some embodiments, separating the plurality of cells comprises trypsinizing the plurality of cells. Other enzymes that disrupt the extracellular matrix of the plurality of cells can also be used to separate the cell. These enzymes include, but are not limited to, catalase, collagenase, elastase, and pancreatin. Any other suitable methods can be used to separate the plurality of cells into single cells.

Any suitable culture medium can be used in the methods described herein. In some embodiments, the culture medium is a biological fluid or a liquid extracted from particular tissues or glands. In some embodiments, the culture medium comprises blood, plasma, or lymph fluid. In some embodiments, the culture medium is an artificial medium. In some embodiments, the culture medium is a balanced salt solution. In some embodiments, the culture medium is a complex medium. In some embodiments, the culture medium is Roswell Park Memorial Institute (RPMI). In some embodiments, the culture medium is Dulbecco's Modified Eagle Medium (DMEM).

Systems for Deterministic Culturing of Selected Single Cells

Also provided herein are systems, e.g., automated systems, for deterministic culturing of selected single cells. Specifically, the systems can be used for selecting and positioning single cells onto the three-dimensional culturing islands. Furthermore, the systems can be used to extract the multi-cell tissue and re-culture the single cells from the multi-cell tissue. In some embodiments, the system is a microfluidic device, and the single cell is selected using a microfluidic device. In some embodiments, the single selected cell is seeded onto the culturing island using a microfluidic device.

In general, the systems include a culture vessel for housing a three-dimensional culturing island made of a matrix attached to a surface of the culture vessel and in contact with a culture medium, wherein one or more parameters of each of the matrix and the culture medium are selected by the user, based on one or more micro-environment selection criteria, what can be selected by a user or can automatically be selected by the system, based on input by a user.

The system includes a cell picking system, e.g., an automated cell picking system, which includes a visualization system, e.g., a microscope, and a single cell retrieval device, e.g., a micropipette and suction system as described in further detail below, arranged for selecting a single cell from a population of cells using one or more cell selection criteria. The selection criteria can be programmed into a control system, which can be selected by a user, e.g., via a keyboard or touch screen, or other input system.

The system can further include a robotic system for supporting and controlling the single cell vacuum device to retrieve and seed the single selected cell onto the culturing island; and optionally a culture medium distribution system, to apply culture medium in an amount sufficient to submerge the seeded single cell and the culturing island in the culture medium.

The system can include a control system for automatically controlling the cell picking system, single cell retrieval device, and robotic system for automatically selecting a single cell according to the selection criteria, e.g., programmed cell selection criteria, and automatically seeding the single cell on the culturing island, e.g., produced according to micro-environment selection criteria, e.g., programmed micro-environment selection criteria, and to control culturing conditions, e.g., automatically, for a time sufficient to grow a multi-cell tissue from the single cell.

Figure 3:
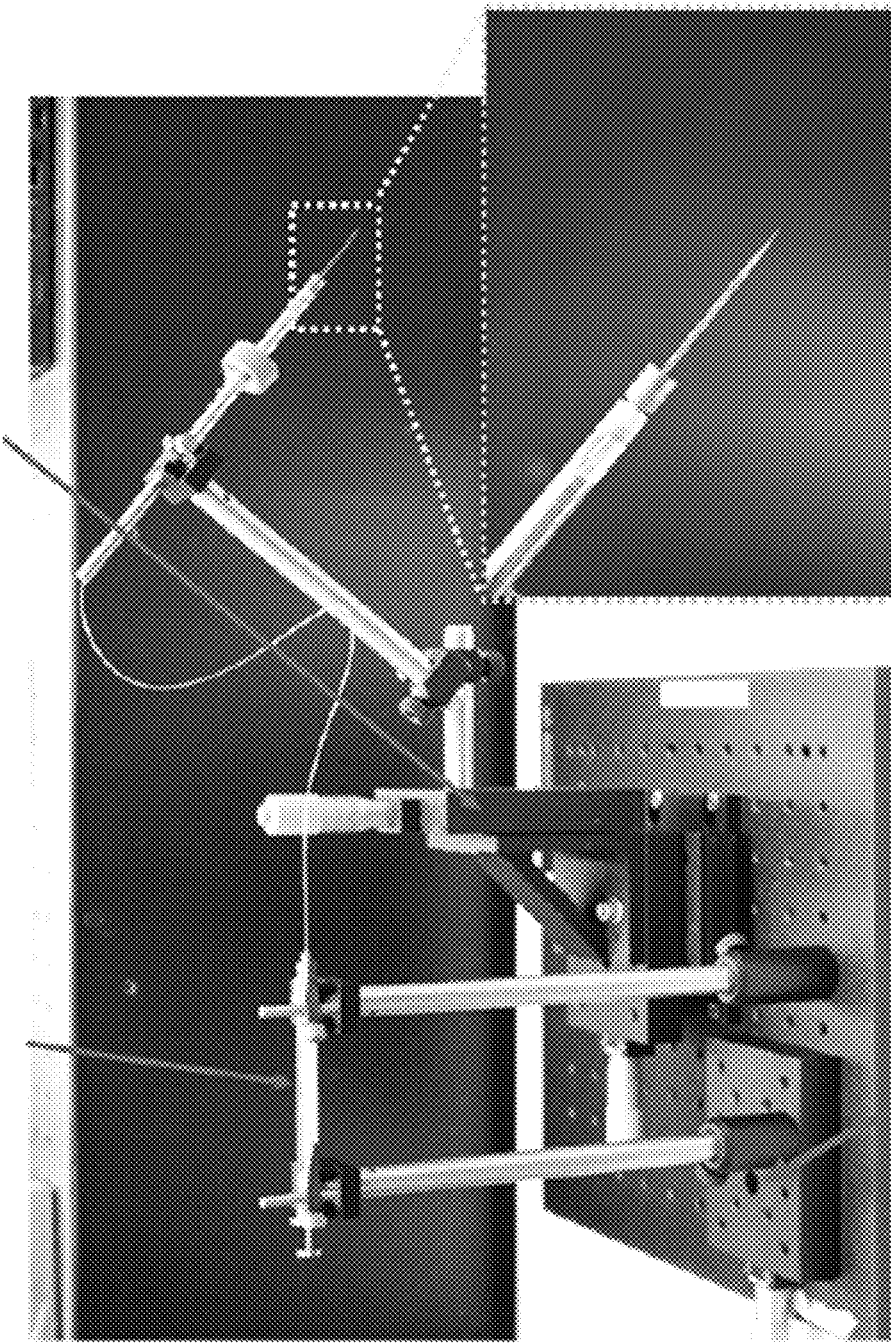
FIG. 3 is an image of a microfluidic system for deterministic single cell picking and placement, with an inset that shows an enlarged portion of a glass micropipette used for cell aspiration and transfer.

As one example shown in FIG. 3, the cell picking system can include a microfluidic device that includes a hollow micropipette, e.g., a glass capillary micropipette tip, a device to hold and position the micropipette, e.g., a 3-axis translational stage for accurate movement of the pipette tip, and a syringe or pump to move small amounts of fluid into and out of the micropipette. In one embodiment, this syringe can be a 250 µl airtight SGE glass syringe with a Luer-Lock®. The micropipette is attached to an adapter, which in turn is attached to the syringe or pump via tubing, e.g., polytetrafluoroethylene (PTFE) tubing. The syringe can also be fitted with a unidirectional translation stage for precise control of flow. Alternatively, the syringe can also be operated with a syringe pump, or a pump can be used with the micropipette directly, without the use of a syringe.

In some embodiments, the system is configured to manually pick up and dispense nanoliter volumes of liquid. In some embodiments, the system works with an efficiency of one to two cells/min while transferring a single cell from a dish to a culturing island. In other embodiments, the micropipette can be controlled by a robotic arm for precise positioning, and a computer-controlled pump or syringe to control the movement of fluids into and out of the micropipette.

In some embodiments, an automated system that has an onboard microscope can scan the candidate cells for seeding, based on selection criteria discussed above, guided by an artificial intelligence (AI)/machine learning (ML)/deep learning (DL) algorithm. The micropipette can then be moved in a computer-controlled fashion to the location of the candidate cell to be picked as seed. The seed can then be moved to and dispensed on an island located in a culturing container (e.g. dish) automatically. The automated system can also be configured to replenish or change the culturing medium in the culturing dish. In some embodiments, the automated system can monitor the growth of the tumors and recognize the growth pattern in accordance with an AI/ML/DL algorithm. Upon the completion of the culturing, the automated system can then detach a tumor from the island and place it in another container or substrate (e.g. another dish or a glass slide or a microchip) for further analysis.

In some embodiments, the hollow capillary tube has an inner diameter of about 5 µm to about 5 mm. In some embodiments, the diameter of the hollow capillary tube has an inner diameter of about 10 µm to about 50 µm.

In some embodiments, a single cell can be seeded on top of a culturing island by releasing the cell with very small quantity of fluid, e.g., culturing medium, and letting the cell adhere to the top of the culturing island. In some embodiments, a single cell can be seeded by penetrating the matrix in the culturing island with the capillary tube and then releasing the cell inside the island with a small amount of fluid. This ensures that the cell is completely embedded inside the matrix. Then the capillary is withdrawn carefully without disturbing the island.

Methods of Generating Tumor Models by Deterministic Culturing

Also provided herein are methods of generating tumor models by deterministic culturing. Specifically, the methods provided herein can be used to generate tumor models that each originates from one cell. Such tumor models can be used to elucidate heterogeneity within a tumor generated by the proliferation of one given cell, as well as the heterogeneity among tumors obtained from different single cells. This approach can, in turn, enable the quantitative measurement of phenotypic variability caused by the microenvironment as well as variability that is intrinsic to a given population of cells. The methods described herein provide critical information that can be used for diagnosis, prognosis, and/or treatment of the tumor.

In some embodiments, the selected single cell is a tumor cell. Any suitable tumor cell can be used in the methods described herein. The tumor (or cancer, used interchangeably herein) can be, for example, acute lymphocytic leukemia (ALL), acute myeloid leukemia (AML), adrenal cancer, anal cancer, basal and squamous cell skin cancer, bile duct cancer, bladder cancer, bone cancer, brain and spinal cord tumors in adults, brain and spinal cord tumors in children, breast cancer, breast cancer in men, cancer in adolescents, cancer in children, cancer in young adults, cancer of unknown primary, Castleman disease, cervical cancer, chronic lymphocytic leukemia (CLL), chronic myeloid leukemia (CML), chronic myelomonocytic leukemia (CMML), colorectal cancer, endometrial cancer, esophagus cancer, Ewing family of tumors, eye cancer (ocular melanoma), gallbladder cancer, gastrointestinal neuroendocrine (carcinoid) tumors, gastrointestinal stromal tumor (gist), gestational trophoblastic disease, Hodgkin lymphoma, Kaposi sarcoma, kidney cancer, laryngeal and hypopharyngeal cancer, leukemia, leukemia in children, liver cancer, lung cancer, lung carcinoid tumor, lymphoma, lymphoma of the skin, malignant mesothelioma, melanoma skin cancer, Merkel cell skin cancer, multiple myeloma, myelodysplastic syndromes, nasal cavity and paranasal sinuses cancer nasopharyngeal cancer, neuroblastoma, non-Hodgkin lymphoma, oral cavity and oropharyngeal cancer, osteosarcoma, ovarian cancer, pancreatic cancer, pancreatic neuroendocrine tumor (NET), penile cancer, pituitary tumors, prostate cancer, retinoblastoma, rhabdomyosarcoma, salivary gland cancer, skin cancer, small intestine cancer, soft tissue sarcoma, stomach cancer, testicular cancer, thymus cancer, thyroid cancer, uterine sarcoma, vaginal cancer, vulvar cancer, Waldenstrom macroglobulinemia, or Wilms tumor.

In some embodiments, the tumor cell(s) are isolated from a subject having the tumor. The subject can be a human or a non-human animal. In some embodiments, the single cell (e.g., tumor cell) is isolated from a patient. In some embodiments, the multi-cell tissue is a tumor tissue, for example, a tissue of any tumor described herein.

In some embodiments, selected cells from the same sample, e.g., circulating tumor cells (CTCs) from a blood sample are seeded on different culturing islands in the same culture vessel. For instance, differential handling of cells from the same sample can be useful for studying organotropism of cancer cells (see, e.g., Chen et al., "Organotropism: new insights into molecular mechanisms of breast cancer metastasis," *NPJ Precision Onc.*, 2, 4, 2018). It is known that CTCs react differently to the conditions around them, thus often metastasizing to one organ rather than another. The deterministic culturing protocols described herein allow for choosing different soil and culture conditions for CTCs from the same sample, because each cell is treated individually.

In some embodiments, one or more parameters of each of the matrix and the culture medium are selected by the user based on one or more cancer microenvironment selection criteria.

In some embodiments, the parameters of the matrix are selected based on a selected cancer micro-environment. For example, a subgroup of CTCs from a blood sample of a breast cancer patient can be seeded in extra-cellular conditions that are similar to brain while other CTCs from the same sample may be seeded in extra-cellular conditions similar to lung, liver, or bone.

In some embodiments, the parameters of the culture medium are selected based on a cancer micro-environment. For example, single cells are seeded in different culture dishes and supplied with different compositions of the culture media. Different dishes may also be supplied with different biochemical factors that affect proliferation and/or differentiation of cells. In some embodiments, cells from breast cancer patients can be seeded on liver like biomaterial and supplied with CXCR4, CXCL12, Interleukin IL-6, Integrin Complexes $\alpha 2\beta 1$, $\alpha 5\beta 1$, N-cadherin HIF-regulated genes LOX, OPN, VEGF, TWIST, to model liver metastasis specially for HER-2 enriched, or ER-positive, or Luminal B or Luminal-HER2 subtypes of cancer. In some embodiments, cells from breast cancer patients can be seeded on bone like biomaterial and supplied with growth factors IGF-1, PGE2, TGF, PDGF, FGF2, Interleukins IL-6, IL-11, IL-1, PTHrP, OPN, Heparanase, to model bone metastasis especially for Luminal-HER2 subtypes of cancer. In some embodiments, cells from breast cancer patients can be seeded on brain like biomaterial and supplied with ST6GALNAC5, growth factors VEGF and HBEGF, CXCR4 chemokine, CK5, MMP1 and MMP-9 cytokine, Interleukin IL-8, Ang-2, COX2, L1CAM to model brain metastasis specially for HER-2 enriched, or Luminal-HER2, or TN-nonbasal or basal-like subtypes of cancer. In some embodiments, cells from breast cancer patients can be seeded on lung like biomaterial and supplied with growth factors and their receptors TGFβ, EGFR, EREG, VEGF, Matrix metalloproteinase MMP-1, MMP-2, COX2, LOX, BMP inhibitors GALANTs and Coco to model lung metastasis specially for TN-nonbasal, or Basal-like, or Luminal B or HER2+, HR− or p53 subtypes of cancer. In some embodiments, cells from breast cancer patients can be seeded on lymph-node like biomaterial and supplied with kallikreins KLK10, KLK11, KLK12, KLK13 to model distant lymph-node metastasis specially for HER-2 enriched, or Luminal subtypes of cancer. The molecular mechanism of breast cancer metastasis is described in, e.g., Chen et al., *NPJ Precision Onc* 2, 4, 2018. In some embodiments, breast cancer cells secreting more VEGFA and IL-8 can be seeded on biomaterial having an artificial microenvironment that is similar to that of brain.

In some embodiments, single cancer cells are selected from a population of cells (e.g., cancer cells or non-cancer cells) using one or more criteria. These criteria include, but are not limited to, the expression level(s) of cell-surface molecules or markers, e.g., cancer antigens, the morphology of the cells, size, aspect ratio, circularity and shape of cells, stemness and proliferation potential of the cells, morphology of the nucleus (size, circularity), presence of nuclear foci, genetic composition, epigenetic modifications, and the secretion of one or more cytokines or chemokines by the cells.

In some embodiments, multiple numbers and types of cells are seeded and co-cultured with single cell precision based on the criteria described herein. For example, one breast cancer cell and one mesenchymal stem/stromal cell can be seeded to study cell engulfment, or one breast cancer cell and two mesenchymal stem/stromal cell can be seeded to study preferential or sequential engulfment.

The applications of the tumor models generated using the methods described herein include functional analyses such as drug testing, biodynamic imaging, studying long-term culturing, and morphological analysis; genetic analyses such as DNA sequencing and RNA sequencing; and immuno-marker-based staining for heterogeneity in drug response within and between tumors, stemness analysis, and proliferation immune analysis.

Methods of Testing Multiple Therapeutic Agents in Deterministic Tumor Models

This disclosure also provides methods of testing multiple therapeutic agents on deterministic tumor models. The methods described herein generate tumor models that can be used for the testing and development of anti-cancer therapies.

In some embodiments, the methods described herein can be used for screening anti-cancer therapies. In some embodiments, the methods described herein can be used for testing one or more therapeutic agents for cancer.

In some embodiments, the methods described herein further include administering one or more anti-cancer therapies to the multi-cell tissue (e.g., a tumor tissue). In some embodiments, the methods described herein further include retrieving one or more multi-cell tissues (e.g., tumor tissues) from the culturing island. In some embodiments, the methods described herein further include separating the cells in a multi-cell tissue (e.g., tumor tissue) into single cells and re-culturing one or more single cells on individual culturing islands. In some embodiments, the methods further include selecting a single cell prior to the re-culturing.

Any suitable therapeutic agents can be tested using the methods described herein. In some embodiments, the therapeutic agent is an anti-cancer agent, for example, an alkylating agent, an antimetabolite agent, an antibody, a hormone, and/or a small molecule compound. In some embodiments, the anti-cancer agent is paclitaxel.

EXAMPLES

The invention is further described in the following examples, which do not limit the scope of the invention described in the claims.

Example 1: Single Cell Culture at Registered Locations on Collagen I Islands Reveals Survival, Proliferation and Tumor Formation Potentials Cell Line and Culture Medium We initially performed characterization experiments under standard 2D cell culture conditions to identify a cancer cell line with which to develop and test the deterministic 3D culturing method. Ten to 20 wells of a 96 well plate received one cell from breast (MCF-7), cervical (KB) and pancreatic cancer (LNCaP) cell lines in culture medium including 10% fetal bovine serum. Approximately 100 cells were seeded in a single well of the same 96 well plate from the same populations of cells as control. At least 50% of the single cells after seven to eight days of seeding had led to a small colony of cells (for all cell lines tested). The MCF-7 cell line was selected to pursue the development of the single cell 3D culture method in light of their high survival rate (95%). These cells are classified as luminal A type of breast cancer cells (estrogen receptor and progesterone receptor positive). This subtype of breast cancer is mostly nonaggressive, and in 3D cell culture MCF7 cells typically form tumors that rarely present invasive extensions or migratory patterns.

For cell culturing, MCF-7 cells (American Type Cell Culture, Manassas, VA) were cultured in RPMI 1640 medium (ATCC) with 10% Fetal Bovine Serum (ATCC). Caco-2 cells were cultured with DMEM medium (ATCC) with 20% Fetal Bovine Serum and other additives (Final concentrations: 4.5 g/L Glucose, 10 mM HEPES, 44 mM Sodium Bicarbonate, 1 mM Sodium Pyruvate, 100 μM non-essential amino acids, 50 mg/L Gentamycin Sulfate, 100 U/L Penicillin, 100 U/L Streptomycin, 2 mM Glutamine, pH 7.2). MDA-MB-231 cells (ATTC) were also cultured in RPMI 1640 medium (ATCC) with 10% Fetal Bovine Serum.

Extracellular Matrix

Collagen I was used as the extracellular matrix (ECM) for 3D cell culture because it is the most abundant fibrous molecule surrounding tumors of epithelial origin like carcinomas, and it can be tuned to a desired stiffness to mimic that of cancerous tissues. Conventional matrix-based 3D cultures in standard well plates use a large amount of collagen spread over the area of each well. For standard 3D cell culture applications that use a large number of seed cells per unit volume of the collagen, it is possible to easily identify and image cells or clusters of cells of interest. However, when seeding a small number of single cells, it is challenging to find and image one particular cell that is almost transparent against a large pool of collagen matrix. This challenge is further exacerbated if the seeding location is not referenced, or the cell in question migrates and/or if it is embedded inside the matrix. Microplates, such as 384 and 1056 well plates have smaller wells, which reduces the amount of collagen needed. However, this setting also reduces the amount of culture medium, i.e. nutrients that need to be supplied to the growing tissue. The necessary frequent changes of the culture medium are greatly impeded by the narrow space in these wells, which prevents the user from easily maneuvering a micropipettor. Therefore, we sought to design a method that has an optimal balance of collagen matrix and volume of medium to sustain the growth of tumors from single cells initially deposited in registered locations and enables an easy observation of the growth process.

Specifically, we used the PHOTOCOL UV (Advanced BioMatrix, San Diego, CA) that is a Methacrylated Type I collagen. Depending on the desired volume, and stiffness of 3320 Pa, the lyophilized and Methacrylated Type I collagen was mixed with an appropriate amount of 20 mM acetic acid solution and a neutralization solution, as per the manufacturer's protocol. The mixture was kept on ice to maintain the final solution in liquid state. Drops (5 μl) were added on a culture dish and used for single cell culture as described below. The thermosetting nature of PHOTOCOL helped keep the gel islands fixed onto the culture dish once they were deposited, and the dish was placed in a temperature-controlled incubator.

We opted for small droplets (5 µl) of tunable Methacrylated Type I collagen matrix (referred to as collagen throughout the manuscript) with a Young's modulus of 3320 Pa (representative of increased ECM stiffness measured in invasive ductal carcinomas of the breast) (see, e.g., Acerbi et al., Integr. Biol. 7, 1120-1134, 2015) placed in a 35 mm polystyrene dish not treated for cell culture (FIG. 1). Up to 50 droplets of matrix were deposited in the dish to form semi-ellipsoidal islands (FIG. 2A), each with a diameter of approximately 3 mm.

Cell Picking Device

Single cells were seeded on the islands using a cell picking set-up as shown in FIG. 3. The cell picking device was assembled using a glass capillary micropipette tip (Clunbury Scientific LLC, Bloomfield Hills, MI) a 3-axis translational stage for accurate movement of the pipette tip (Thorlabs Inc., Newton, NJ) and 250 µl airtight SGE glass syringe with Luer Lock (FIG. 3). A hollow glass capillary of 50 µm diameter worked as a micropipette. It was attached to an adapter, which in turn was attached to a syringe via Polytetrafluoroethylene (PTFE) tubing. The syringe was also fitted with a unidirectional translation stage for precise control of flow. Alternatively, the syringe can also be operated with a syringe pump. The system was optimized to manually pick up and dispense nanoliter volumes of liquid and work with an efficiency of one to two cells/min while transferring a single cell from a dish to a matrix island.

Single Cell Culture Seeding and Maintenance

Culturing the cells on islands allowed simple tracing of a particular cell by recording still images at various intervals, without continuous time-resolved microscopy that would otherwise be necessary if multiple cells were used (since cells can often migrate over small distances on the surface of collagen).

For single cell culture seeding, approximately 5000 cells from the flask were obtained by dilution and placed in a dish for picking. The cells that ended up on each island were picked from among these 5000 cells. The same culture medium mixed with 1% v/v GIBCO Penicillin-Streptomycin (10,000 U/ml) antibiotic (Life Technologies, Carlsbad, CA) was used to culture single cells. The antibiotic was added to avoid bacterial contamination that can occur when transferring cells onto the matrix island in nonsterile conditions. Five µl liquid drops of collagen matrix were deposited at desired number of spots (up to 50) on a sterile 35 mm polystyrene culture dish (CORNING 430558).

The matrix was allowed to solidify for 30-45 minutes in the same incubator that is used for cell culture (maintained at 37° C. temperature, 5% $CO_2$ concentration and 95% Relative Humidity). After stiffening of the matrix, 2 ml of RPMI 1640 culture medium premixed with 10% v/v fetal bovine serum and 1% v/v GIBCO Penicillin-Streptomycin (10,000 U/ml) antibiotic, pre-heated to 37° C. was introduced in the dish. This was done slowly by placing the pipette tip against the side of the dish to avoid air bubbles and dislocation of the islands. Then the dish was placed into the incubator until cells were ready for seeding. Addition of cell culture medium allowed for the matrix to remain solid without drying out. When it was time to seed the cells, 1.8 ml of culture medium was removed from side of the dish, which exposed the top of each island while keeping the islands partially immersed to avoid drying.

The cell-picking setup was used to pick and place single cells from another dish to the top of Collagen I islands one at a time, using a microscope. After all the cells were transferred, the dish was covered and placed in the cell culture incubator for 20-30 minutes to allow the cells to stick to the matrix. During this period the surrounding liquid medium at the bottom of the dish provided enough moisture to avoid drying. At the end of this period of time, 1.8 ml culture medium with 1% v/v antibiotic was replenished gently, and the culture dish was returned into the incubator.

The culture medium was changed every 5-7 days initially with single cells and when the tumors were small, and more frequently (every 2-3 days) as tumors became larger. Removing and adding medium was performed from the side of the culture dish to avoid turbulence.

Cell Survival and Proliferation Efficiency

Once a cell is seeded on top of a collagen matrix island, there are two possible immediate outcomes; the cell may successfully bind to the collagen gel or it may not bind and float away. If the cell binds to collagen, it may or may not survive, and if it survives, it may (epi)genetically be predisposed to proliferate or find the culture conditions unsuitable for proliferation. To study the reproducibility of these outcomes, three biological replicates of the cultures (i.e., using three different batches of MCF7 cells) were performed. Collagen matrix islands were spotted on 35 mm dishes with the number of islands in each dish varying between 25 and 50. Each island was seeded with exactly one MCF-7 cell on Day 0 and observed on Day 1 to 2 to check for cell attachment and again on Day 9 to 10 to check for sustained attachment and proliferation under an upright microscope in bright-field mode.

Hoechst staining was used to visualize cells in the tumor using fluorescence microscopy (FIG. 4). Specifically, cells were washed in PBS and fixed in 4% paraformaldehyde before staining with 1:1000 PBS diluted solution of 20 mM Hoechst 33342 (Thermo Fischer Scientific, Waltham, MA) for 10 minutes. After washing once with PBS, tumors were imaged with a ZEISS LSM 800 confocal microscope with an excitation laser of 401 nm wavelength and with 10× magnification lens (EC Plan-Neofluar® 10×/0.30 M27). Brightfield and fluorescence images were also obtained using NIKON ECLIPSE® 80i upright fluorescence microscope, which were used to analyze the morphology of the tumors with ImageJ. Z-stacks were obtained for each tumor at a Z-step size equal to half of the depth of field which was 14.5 µm (using objective: EC Plan-Neofluar® 10×/0.30 M27).

For each tumor, dead and live nuclei at every alternate plane of the z-stack were manually counted using Fiji cell counting software. Each alternate plane of the Z-stack was skipped to account for the overlap in signal due to depth of field being twice that of Z-step size. This approach allowed for better resolution images and prevented any double counting of cells. A similar approach was used for the assessment of nuclear morphometry after manual segmentation with Fiji.

As shown in Table 1, a great majority of the islands (83% to 98%) successfully retained a single MCF7 cell (the first column is the total number of islands in each dish that were seeded with a single MCF-7 cell on Day 0; the second column shows the percentage of islands each having a single cell successfully attached after one to two days). As illustrated in the third column of table 1, the percentage of islands with visible cells nine to 10 days after seeding was lower than at day 1; it might be due to cell death in the first few days of culture or detachment of the cells. The cell clusters that were visible on the islands at the end of the observation period varied in size.

In summary, over the three biological replicates, 81-94% of the islands had visible cells (nonproliferating or organized into tumors; column 3 of Table 1) and 66-81% of the islands harbored tumors larger than 5000 µm² (column 4 of Table 1), indicating that the cells that seeded these tumors had a strong proliferation potential. From this first set of observations, it could also be concluded that individual cells that came from the same nominal (MCF7) population displayed different potentials to survive and proliferate to form tumors.

TABLE 1

Cell survival and proliferation efficiency: Percentage of total number of islands

|  | Total number of | Islands with a cell on day 1 to | Islands with visible cells on | Islands with tumors of area >0.005 mm$^2$ |
| --- | --- | --- | --- | --- |
| Exp. 1 | 26 | 96% | 92% | 77% |
| Exp. 2 | 48 | 98% | 94% | 81% |
| Exp. 3 | 47 | 83% | 81% | 66% |

Figure 5A:
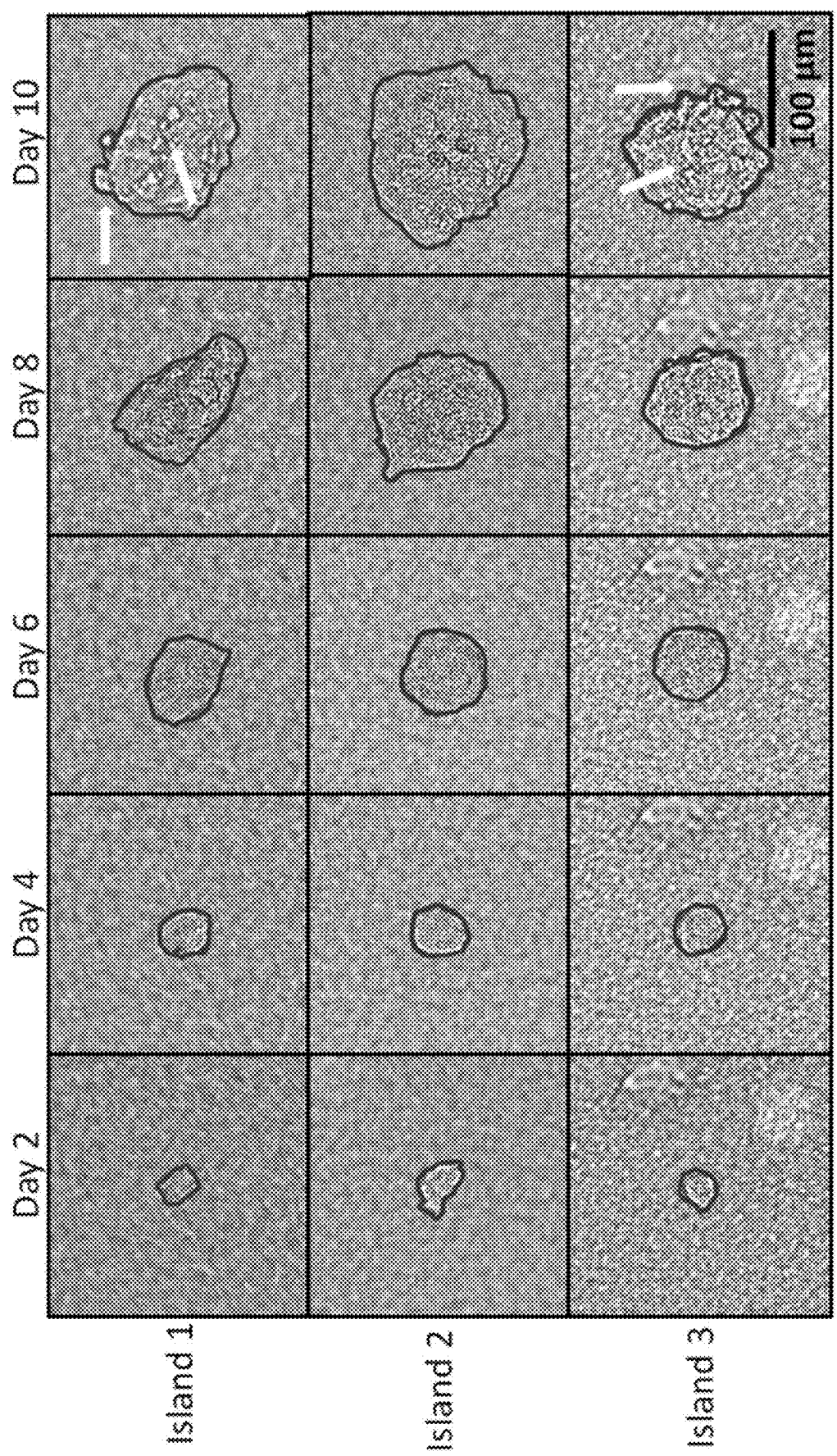
FIG. 5A is a series of bright-field images of three tumors (Islands 1, 2, and 3) over time (Day 2 to Day 10). Grape-like features on the tumor top and at the periphery are indicated by white arrows at Day 10.
Figure 5B:
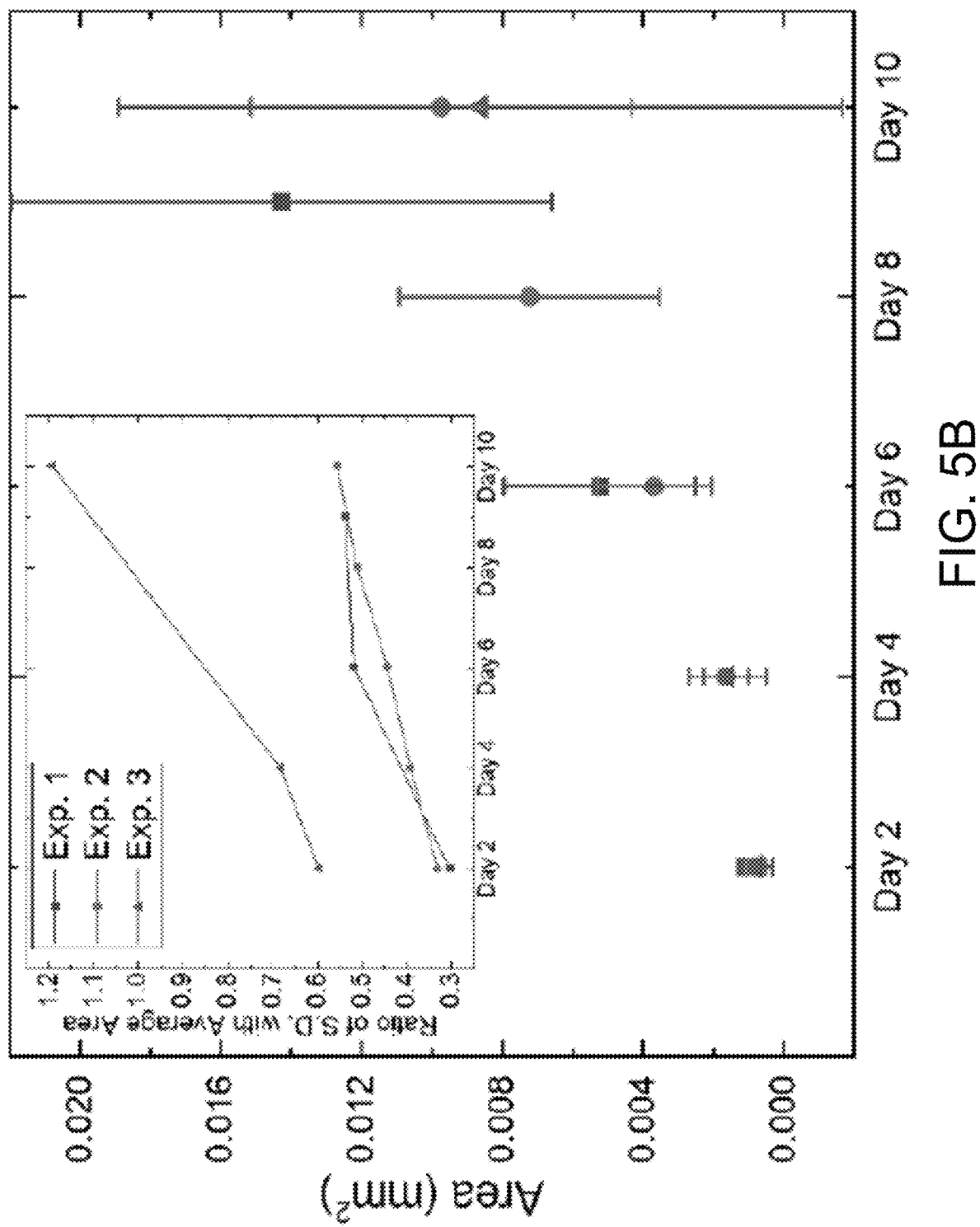
FIG. 5B is a graph that shows temporal evolution of tumor area over 10 days for three biological replicates. Each solid square represents the average area of 26 tumors, each solid circle represents 48 tumors, and each triangle represents 47 tumors with standard deviations. The inset shows the increasing trend in ratio of standard deviation to the average of tumor area for each experiment over time.
Figure 5C:
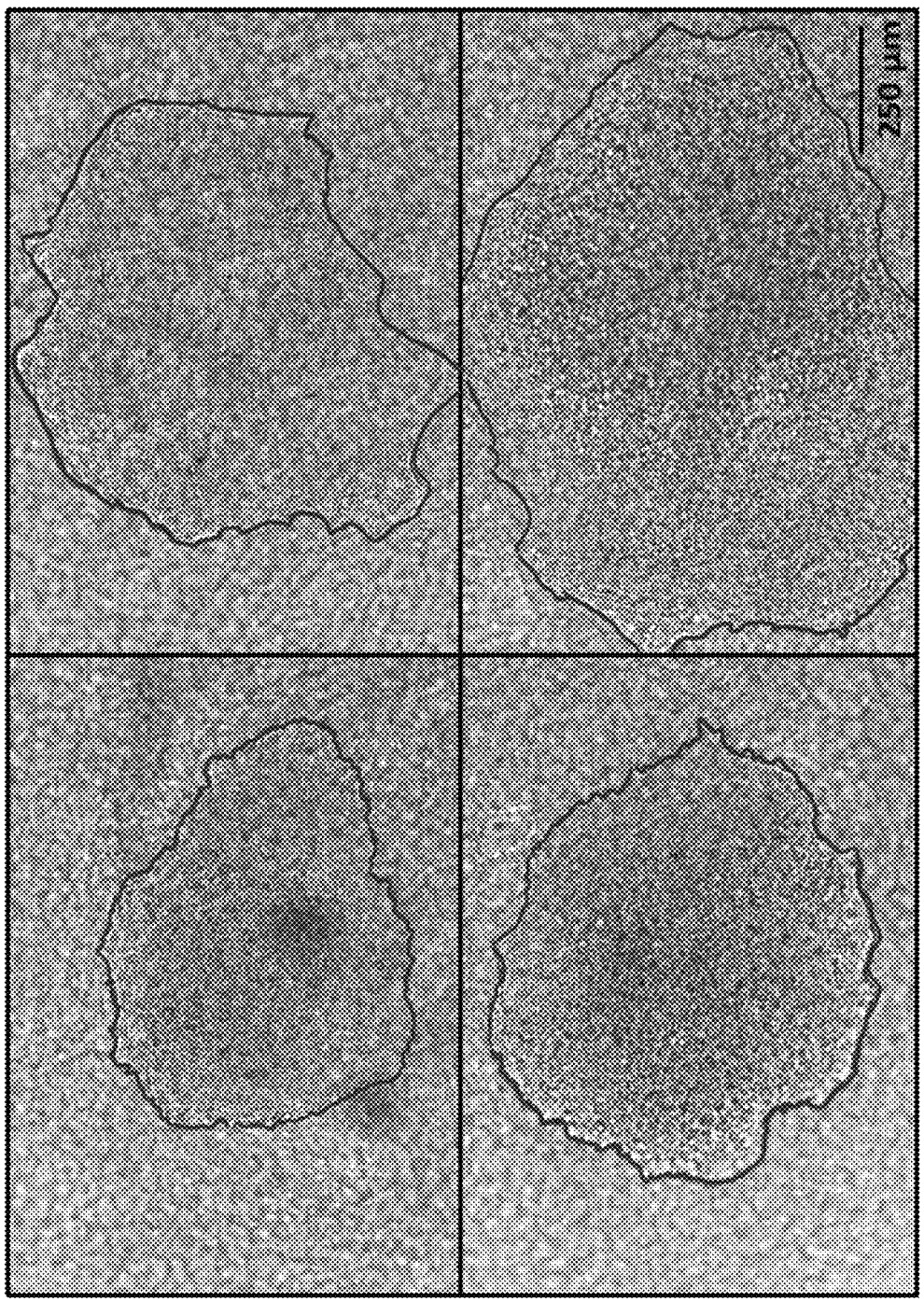
FIG. 5C is a series of microscope images of tumors that were maintained in culture for 21 days.

Example 2: Single Cell-Derived Tumors are Reminiscent of the Cancer Type and Reproduce Inter-Tumor Heterogeneity An advantage of the methods provided herein is the inherent efficacy in tracking the behavior of a single cell at the beginning of the culture period. Locating and recognizing the cell on the collagen island is a rapid process, even if the cell migrates over small distances. Similarly, changes in the appearance of multicellular clusters and tumors can be made using bright-field upright microscopy. Hence, the cells can be observed by a sequence of still images, (as opposed to monitoring multiple cells using continuous time-resolved microscopy) as shown by multiple examples of a single MCF-7 cell evolving into a tumor (FIGS. 5A-5C). Islands 1 and 3, for instance showed grape-like features on the tumor top and at the periphery, while for the tumor on island 2 the top surface appeared regular or smooth (FIG. 5A).

All experiments showed an increase in tumor size based on the duration of culture, but with increasing disparity among tumors (FIG. 5B). In cultures kept for 20 to 25 days, some tumors continued to grow and cover most of the collagen island's top surface, with a diameter above 500 µm (FIG. 5C). Very few tumors (on average two out of 30) displayed a dark central region. When observed under fluorescence, these regions were faintly colored in red after treatment with Propidium Iodide, confirming necrosis (see, e.g., Mehta et al., Opportunities and challenges for use of tumor spheroids as models to test drug delivery and efficacy, 2012, doi:10.1016/j.jconrel.2012.04.045). Thus, cultures should be stopped before tumors reach 400 µm in size since the maximum penetration depth of nutrients and oxygen is ~200 µm. All analyses for the rest of the experiments were performed with 10-14 days old 3D cultures and tumors below 400 µm.

To determine the extent for the single cell culture on collagen I-island approach to recapitulate the characteristics of different types of cancer, we also tested the method with Caco-2 cells that represent a poorly aggressive colorectal carcinoma. Bright-field images obtained on day 10 of culture show that only 30% of the single cells led to tumor formation. Moreover, the rate of tumor growth seemed slower in comparison to the MCF-7 cells for the same ECM conditions, as illustrated by the smaller area of the tumors (FIGS. 6A-6B) although it is noteworthy that these cultures were not done in parallel with those of MCF7 cells. Importantly, for both MCF7 and Caco-2 cells, the sizes and shapes of tumors varied considerably. Arm-like extensions often reveal the invasive nature of tumors (see, e.g., Paszek et al., Cancer Cell 8, 241-254, 2005; and Albini et al., Cancer Research 47, 1987). These features were very rarely observed, but one tumor (out of 15 for MCF7 cells and out of six for Caco-2 cells) for each cancer type appeared fragmented (i.e., as if one or more cells migrated away from the main tumor to create a secondary tumor; see island xii in FIG. 6A & island 2 in FIG. 6B).

Tumors produced by individual Caco-2 cells looked different from tumors produced by individual MCF7 cells. For most Caco-2 tumors, remarkable features included more angular shapes and hollow structures (islands 1, 2, 6, 7) reminiscent of glandular-like adenocarcinoma seen in vivo (see, e.g., Fleming et al., *Journal of Gastrointestinal Oncology* 3, 153-173, 2012) (FIG. 6B). Interestingly, highly aggressive MDA-MB-231 cells that represent triple negative breast cancer subtype, did not form tumors (i.e. an actual growth into a mass). Instead, the cells proliferated, but moved away from each other while remaining attached to the matrix island. The aggressive nature of these cells was expressed via their migratory behavior and spindle-like shape revealing a mesenchymal phenotype).

In light of the apparent heterogeneity in tumor development (which was illustrated by tumors growing into different sizes and shapes over the same time period), a quantitative assessment was conducted with MCF7 tumors. Three morphometric parameters, namely area, circularity (ratio of area to the square of the perimeter scaled by a factor of 47) and aspect ratio (ratio of major axis to minor axis), were analyzed with Image J (see e.g., Schneider et al., NIH Image to ImageJ: 25 years of image analysis. 2012, doi:10.1038/nmeth.2089). The standard deviation in the parameters was relatively high in all experiments as shown for three replicates of MCF-7 cells. Even when tumors were generated from single cells coming from the same batch and passage of the cell line, and cultured under the same micro-environmental conditions, they differed strikingly from one another in terms of morphometry, revealing intertumor heterogeneity (FIG. 5B).

Similar results were observed with Caco-2 cells. Only moderately negative (Circularity vs. Aspect Ratio: Pearson Correlation Coefficient: −0.66) or no correlation (Pearson Correlation Coefficient: −0.14 and 0.016 for Tumor Area vs. Aspect Ratio and Tumor Area vs. Circularity, respectively) was observed between any two of the three parameters in MCF7 tumors. Moreover, the depth of MCF-7 tumors measured after 14 Days in culture using confocal microscopy, was on average 75 µm in the z-dimension with a standard deviation of 19.7 µm, suggesting that there is significant variation in the number of layers of cells (a cell is on average ~15 µm in size) for the structures produced on the islands of collagen I.

The degree of heterogeneity in MCF7 tumor sizes was paralleled by heterogeneity in response to Paclitaxel, a commonly used cytotoxic drug for the treatment of breast invasive ductal carcinoma, for which luminal A breast cancers may show different levels of sensitivity depending on the tumor phenotype (see, e.g., Zhang et al., *Oncotarget* 7, 5702-5714, 2016). Thirteen-day old tumors were treated with three different concentrations of Paclitaxel (5 nM, 20 nM and 100 nM) for 24 hours. The control was a separate dish containing islands seeded with single cells from the same population as the treated dishes and cultured with the same preparation of medium, to which 0.01% DMSO was added in order to match the maximum concentration of vehicle used in drug-treated samples. It is widely known that cells undergoing apoptosis exhibit a distinctive nuclear morphology as compared to healthy and necrotic cells (see, e.g., Crowley et al., *Cold Spring Harb. Protoc.* pdb-.prot087205 2016). Hence, tumors were treated with Hoechst 33342 nuclear dye to calculate the percentage of cells undergoing apoptosis based on nuclear morphology.

Since each island comprises a relatively small amount of collagen (e.g. as opposed to an entire well of a 96-well plate), excess dye that inadvertently diffuses into the collagen can be washed easily to reduce any background fluorescence signal. Live and dead cells (the latter indicated by smaller or fragmented nuclei with intense staining due to DNA condensation) from individual planes of z-stack confocal images of each tumor were manually counted according to a procedure described by Crowley et al. (see, e.g., Crowley et al., *Cold Spring Harb. Protoc.* pdb.prot087205 2016). As expected, the average cell death increased with drug concentration, starting with cell death at 2.9% for the control sample (FIGS. 9A-9B). Interestingly, there was a significant variation in the response of individual tumors for each drug concentration, confirming intertumor heterogeneity. In conclusion, although tumors from the cell population display some of the main characteristics of the type of cancer from which they originated, there are significant phenotypic variations among tumors produced by cells that are individually picked from this population.

Example 3: Tumor Size Positively Correlates with Intra-Tumor Heterogeneity and Nuclear Size in Luminal A Type of Breast Cancer Results related to tumor size and shape presented above deserved a particular attention in terms of possible new biological information. We investigated whether the variation in tumor size and shape formed by individual cells from the same initial population might be an indication of phenotypic heterogeneity. Pathologists have relied on simple nuclear morphometric features such as size (or area) and shape (or circularity) for decades to determine tumor aggressiveness. We have also applied this method to assess tumor progression in 3D cell culture of preinvasive breast cancer cells (see, e.g., Chittiboyina et al., *ACS Biomater. Sci. Eng.* 4, 432-445). The nuclei from six MCF-7 tumors at day 14 of culture, from the same biological replicate (i.e., seeding cells were from the same cell culture flask), were stained with Hoechst and imaged by confocal microscopy.

Analysis was performed with Fiji (see, e.g., Schindelin et al., *Nature Methods* 9, 676-682, 2012) for nuclear area and circularity and was compared to the area and circularity of the corresponding tumors. To analyze the variation in nuclear area and nuclear circularity for heterogeneity analysis, the sample standard deviation formula in MS EXCEL was used. Pearson Correlation coefficient function of MS EXCEL was used to study correlation between every two of the following six parameters: tumor area, tumor circularity, average nuclear area, average nuclear circularity, standard deviation of nuclear area, standard deviation of nuclear circularity. Violin plots for nuclear area and nuclear circularity were created using the ORIGIN(Academic), Version 2019b, OriginLab Corporation, Northampton, MA.

A two-tailed heteroscedastic (unequal variance) T-test was used to compare the percentages of cell death between tumors treated with different concentrations of Paclitaxel (Comparisons were made between 0 nM & 5 nM; 5 nM & 20 nM; 20 nM & 100 nM). A similar test was used to check statistical difference between the three replicates for comparing tumor morphologies.

Figures 7A, 7B:
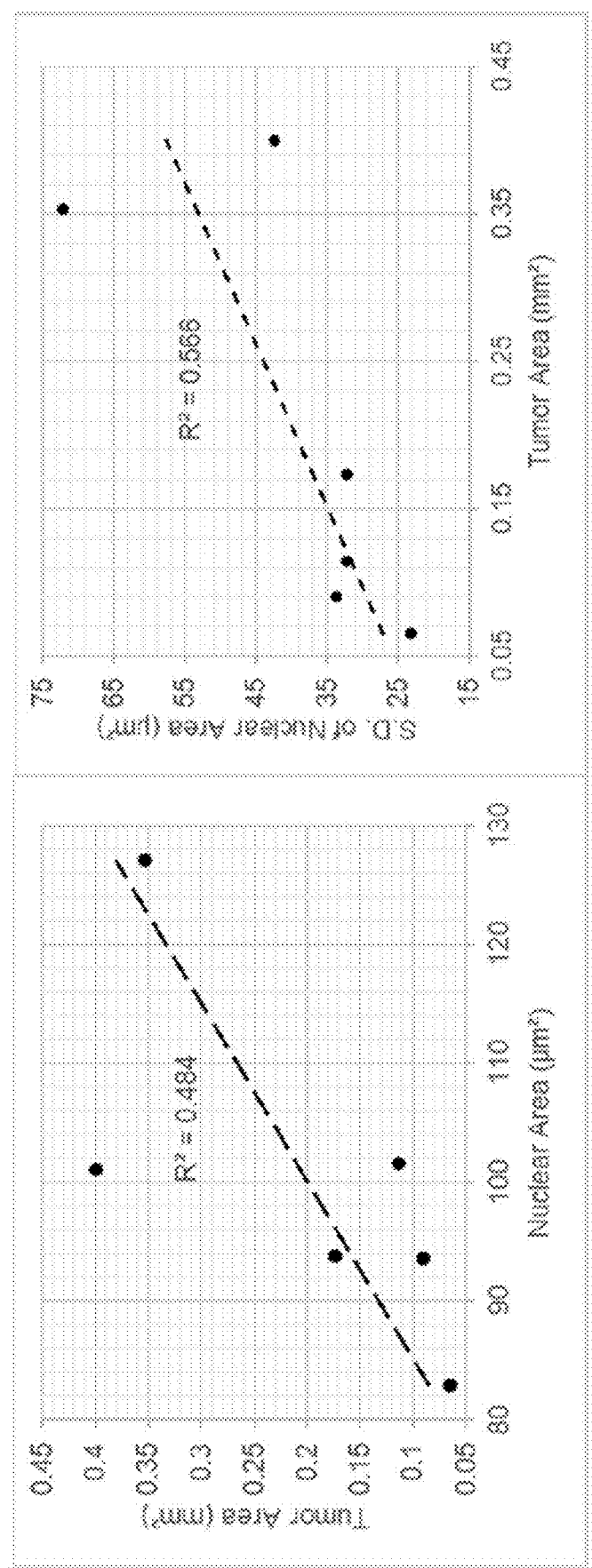
FIGS. 7A-7B are graphs that show trendlines and associated R-square for the fit with high positive Pearson correlation (r≥0.70, n=6) between nuclear area and tumor area (FIG. 7A) and between tumor area and standard deviation [S.D.] in nuclear area (used as a measure of heterogeneity) (FIG. 7B).

Based on 50-75 randomly selected nuclei for each tumor, there was a significantly positive correlation (Pearson's coefficient correlation r≥0.70) between tumor area and the average nuclear area (i.e., the bigger the tumor, the bigger the nuclei on average in that tumor) (FIG. 7A). We also compared the same morphometric parameters (circularity and area) for each tumor with the standard deviation of the circularity and area of their nuclei, since intratumor heterogeneity has been associated with changes in phenotype (see, e.g., Janiszewska et al., *Oncogene* 39, 2031-2039). There was a significant positive correlation (Pearson's correlation coefficient, r≥0.70) between tumor area and the degree of heterogeneity in nuclear area (FIG. 7B). There was no significant correlation between any other two parameters (i.e. Pearson's coefficient <0.7). The trends in nuclear area and circularity for each tumor are observed in more detail in violin plots (FIGS. 7C-7D). The two tumors with the highest variation in nuclear area (tumors 2 and 4) have a narrow tail, indicating that a small fraction of the nuclei have significantly larger nuclear area. These particular tumors also have the largest area (0.4 and 0.35 mm$^2$).

Hence, this small population of cells might indeed have a causal relationship with large tumor area and may be the chief driver of tumor aggression. Heterogeneity in nuclear area does not always correspond to heterogeneity in nuclear circularity. Higher heterogeneity for nuclear circularity exists in tumors 1, 2 and 6. Especially in tumors 2 and 6, we observe wider distribution of nuclear circularity around the mean of the violin plots indicating amplified heterogeneity. It is possible that the observed differences in intra-tumor heterogeneity influence the variation in tumor area as seen in FIG. 5B.

Retrieval of Tumors

Figure 8:
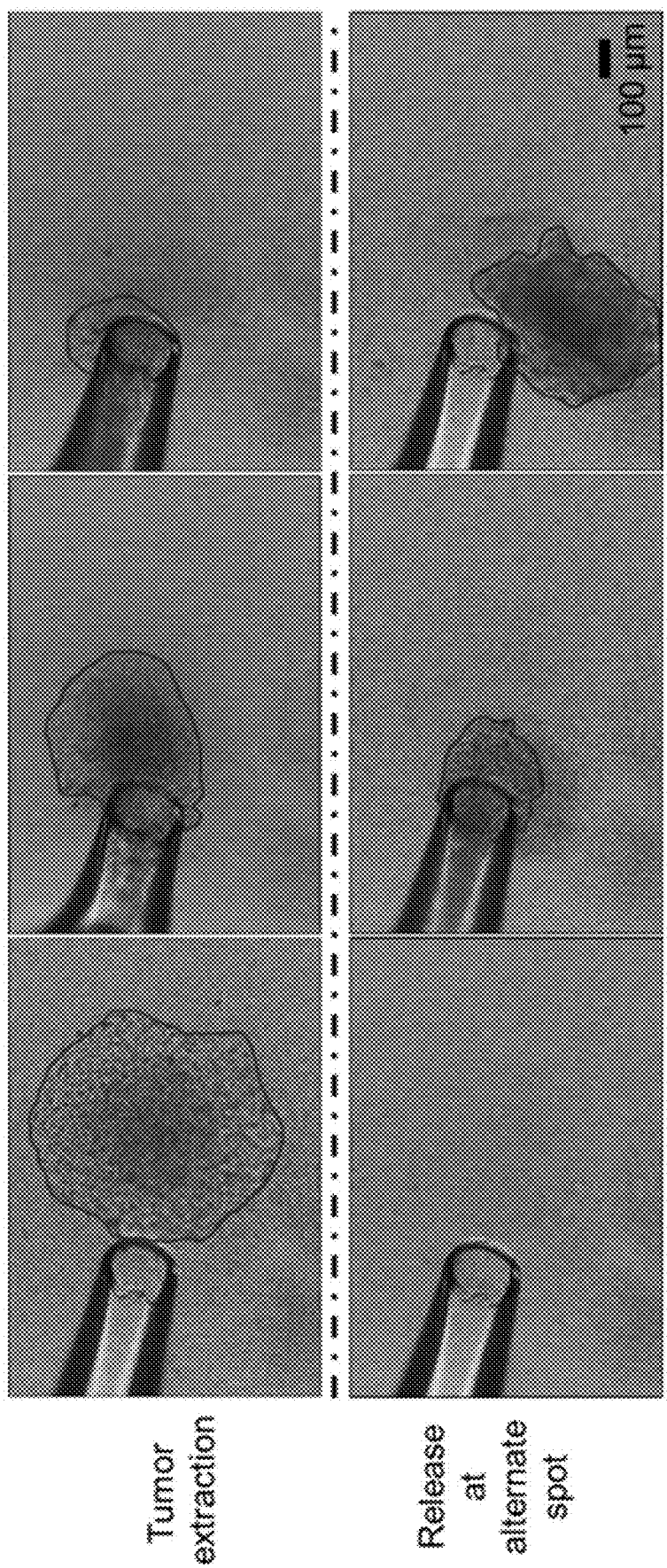
FIG. 8 is a series of microscope successive images that show a tumor being extracted from a collagen island, after 20-30 minute treatment with collagenase, using a glass tip of ~150 µm diameter (top panel); and successive images of the same tumor being released at an alternate location (e.g., for applications such as dissociation and re-seeding of selected single cells from the tumor) (bottom panel). The outline delineates the visible portion of the tumor during different steps of the process.

An additional advantage of culturing tumors on top of collagen islands (instead of inside) is the simplicity of tumor retrieval for further analysis (FIG. 8). To determine whether intra-tumor heterogeneity revealed by nuclear morphometry analysis corresponds to the presence of different cell phenotypes, a 14-day tumor formed by one MCF7 cell was released from the matrix using collagenase and cell/tumor picking setup for transfer.

Specifically, the 3D cultures were treated with collagenase for 20-30 minutes to partially digest the surface of the collagen islands and help detach tumors from the top of the island. A pipette tip of ~150 µm diameter was used for retrieval of tumors of 0.1-0.2 mm$^2$ in size on average, under a microscope. The diameter of the tip was chosen so that it is significantly smaller than the island but similar in size to the tumor in order to retrieve the tumor without accidentally aspirating an entire collagen island. A larger diameter of the tip may be used depending on the size of tumors. Manual control of the picking process permitted more precision for the retrieval of tumors, without breaking them apart.

Re-Culturing of Single Cells from a Tumor

A desired tumor was extracted as described here. Then, 10 µl of Trypsin-EDTA solution was placed in the cap of a small RNA-free tube. The extracted tumor was introduced into the trypsin solution for 5 minutes. The rest of the tube was filled with 100 µl of culture medium with 10% FBS and the tube was centrifuged gently (600 g for 5 seconds) to mix the Trypsin with the culture medium and stop Trypsin activity. The liquid was moved up and down rapidly with a 5 µl pipette to break down the tumor into smaller clusters. All of the liquid was removed and placed in the center of a 35 mm culture dish. Another 500 µl of culture medium was added gently and single cells were picked up as described before.

Figure 10:
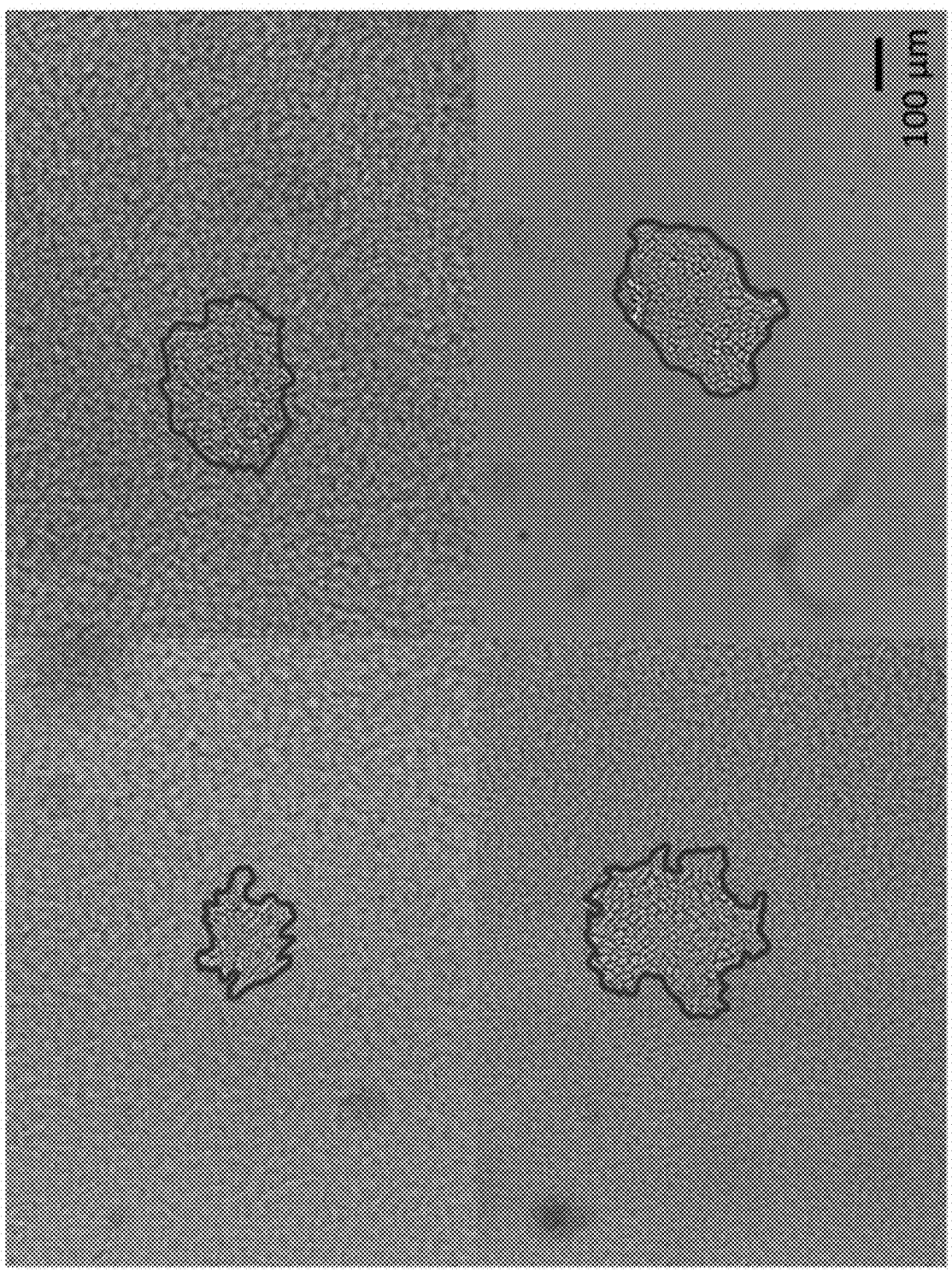
FIG. 10 is a series of Day 10 bright-field images of tumors obtained by re-culturing of single cells after breaking an initial tumor into single cells.

After separation with Trypsin-EDTA, 32 single cells were picked and seeded on new collagen islands. At day 10 of culture, 24 of the islands displayed cells. Measurement of heterogeneity based on size and shape of these second-generation tumors showed high variability in three morphometric parameters (average area: 0.03 mm$^2$ with standard deviation (S.D.) 0.023 mm$^2$, average circularity: 0.49 with S.D. 0.18, and average aspect ratio: 1.75 with S.D. 0.72). Thus, intra-tumor heterogeneity in the first-generation tumor was associated with the formation of second-generation tumors with varied sizes and shapes (FIG. 10).

In conclusion, we have developed a highly efficient and effective method to generate tumors from isolated, individually targeted single cells. Our protocol achieves this goal in a deterministic manner by physically relocating each individual cell from its source to the top of a matrix island. Morphometric analysis of the tumors produced by single cancer cells revealed both inter-tumor and intra-tumor heterogeneity. Notably, comparison of morphometric parameters between tumors and their nuclei demonstrated a positive link between tumor size in luminal A breast cancers and the size of nucleus (based on its average and its variability).

Our approach is cost-efficient, utilizes standard laboratory equipment and consumes low quantity of reagents. Due to the discrete, island-like nature of the collagen support, a cell culture dish of 35 mm uses less than 250 µl collagen matrix and 2 ml of culture medium. This condition eliminates the need to frequently change the medium due to extremely low consumption of nutrients by the tumors. The method is highly amenable for future automation for higher speed, throughput and repeatability both for deposition of collagen islands and for choosing and seeding individual cells. Analyses such as immunomarker based assays, imaging assays, genetic sequencing assays can potentially be performed on the tumors cultured using this method.

The deterministic 3D culturing is highly useful for a range of applications, including propagating extremely rare cells (like circulating tumor cells-CTCs and circulating fetal cells), as well as studying the nature and impact of phenotypic heterogeneity in tumors and tissues. The deterministic aspect of the culture method can be developed in future work via imaging of epigenetic modifications in order to select cells with different epigenetic make-up and follow the resulting tissue formation at registered locations under defined 3D cell culture conditions.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for deterministically culturing one or more single cells into respective multi-cell tissues, the method comprising:
 (a) depositing one or more separate droplets of about 0.1 µL to about 100 µL per droplet of a liquid matrix material onto a surface of a culture vessel to form one or more three-dimensional culturing islands attached to the surface of the culture vessel, wherein each culturing island is separated and not in contact with any other culturing island, and wherein each separate culturing island can comprise one or more droplets of a liquid matrix;
 (b) allowing the matrix material in each culturing island to solidify, or solidifying each culturing island, wherein the one or more culturing islands become solid or semi-solid;
 (c) adding a culture medium to the culture vessel in an amount sufficient to contact, but not completely submerge, each of the culturing islands, wherein the top of each culturing island is not submerged in the culture medium;
 (d) selecting one or more parameters of each of the matrix and the culture medium based on one or more microenvironment selection criteria comprising one or more of chemical composition, stiffness, pH, porosity, or presence of one or more specific molecules that facilitate cell attachment, probe cell proliferation, or cause cells to differentiate into organ-specific cells;
 (e) selecting one or more single cells from a population of tumor cells, stem cells, or fetal cells using one or more cell selection criteria comprising one or more of an expression level of one or more cell-surface molecules, a morphology of the cell, a shape of the cell, a circularity and aspect ratio of the cell, a stemness of the cell, a proliferation potential of the cell, a type of the cell, a morphology of the nucleus, a presence of nuclear foci, a genetic composition, epigenetic modifications, and/or a secretion of one or more cytokines or chemokines by the cells;
 (f) seeding one or more selected single cells onto or into each of the culturing islands, with one single cell seeded per island, and providing a time sufficient to enable the one or more single cells to adhere to a surface of a respective culturing island or adhere to the matrix within the respective culturing island, wherein each of the one or more culturing islands then includes a single cell;
 (g) adding additional culture medium in an amount sufficient to submerge the one or more seeded single cells and the one or more culturing islands in the culture medium; and
 (h) culturing the one or more single cells on or within the one or more culturing islands for a time and under conditions sufficient to grow one multi-cell tissue from each seeded single cell.

2. The method of claim 1, wherein the matrix comprises one or more components of an extracellular matrix, selected from the group consisting of collagen, a gelatinous protein mixture that resembles extracellular matrix, elastin, and laminin.

3. The method of claim 2, wherein the matrix is solidified by cross-linking.

4. The method of claim 1, wherein the diameter of each of the culturing islands is about 1 mm to about 10 mm.

5. The method of claim 1, comprising a plurality of culturing islands.

6. The method of claim 5, wherein a distance between the culturing islands is at least about 1 mm.

7. The method of claim 5, wherein the culturing islands are separated in individual compartments.

8. The method of claim 1, wherein the volume of the culturing medium is about 1.0 µL to about 10 µL.

9. The method of claim 1, wherein the microenvironment mimics a cancer microenvironment.

10. The method of claim 1, wherein each of the single cells is selected and seeded using a microfluidic device.

11. The method of claim 1, wherein the culture medium comprises a biological fluid or a liquid extracted from a tissue or gland.

12. The method of claim 11, wherein the biological fluid is blood, plasma, or lymph fluid.

13. The method of claim 1, wherein the single cell on each respective culturing island is cultured for about 8 to about 11 days.

14. The method of claim 1, wherein each single cell is a single tumor cell.

15. The method of claim 14, wherein the tumor is a colorectal tumor or a breast tumor.

16. The method of claim 14, wherein the single tumor cell is isolated from a patient.

17. The method of claim 1, further comprising separating individual cells from the multi-cell tissue(s) and culturing the separated individual cells.

18. The method of claim 1, further comprising administering a therapeutic agent to the multi-cell tissue(s), thereby testing an effect of the therapeutic agent on the multi-cell tissue(s).

\* \* \* \* \*